United States Patent
Gorochow et al.

(10) Patent No.: US 11,076,861 B2
(45) Date of Patent: Aug. 3, 2021

(54) FOLDED ANEURYSM TREATMENT DEVICE AND DELIVERY METHOD

(71) Applicant: DePuy Synthes Products, Inc., Raynham, MA (US)

(72) Inventors: Lacey Gorochow, Miami, FL (US); Juan Lorenzo, Davie, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 126 days.

(21) Appl. No.: 16/159,582

(22) Filed: Oct. 12, 2018

(65) Prior Publication Data
US 2020/0113576 A1    Apr. 16, 2020

(51) Int. Cl.
*A61B 17/12*    (2006.01)

(52) U.S. Cl.
CPC .. *A61B 17/12113* (2013.01); *A61B 17/12031* (2013.01); *A61B 17/12145* (2013.01); *A61B 17/12177* (2013.01)

(58) Field of Classification Search
CPC ........ A61B 17/12172; A61B 17/12031; A61B 17/12145; A61B 17/12113; A61B 17/12177; A61B 2017/12054
See application file for complete search history.

(56) References Cited

U.S. PATENT DOCUMENTS

| | | | |
|---|---|---|---|
| 2,849,002 A | | 8/1958 | Oddo |
| 3,480,017 A | | 11/1969 | Shute |
| 4,085,757 A | * | 4/1978 | Pevsner ............ A61B 17/12031 604/907 |
| 4,282,875 A | * | 8/1981 | Serbinenko ...... A61B 17/12109 604/907 |
| 4,364,392 A | * | 12/1982 | Strother ............. A61B 17/0057 606/195 |
| 4,395,806 A | | 8/1983 | Wonder et al. |
| 4,517,979 A | * | 5/1985 | Pecenka ........... A61B 17/12109 604/907 |
| 4,545,367 A | | 10/1985 | Tucci |
| 4,836,204 A | | 6/1989 | Landymore et al. |

(Continued)

FOREIGN PATENT DOCUMENTS

| | | |
|---|---|---|
| CA | 2395796 A1 | 7/2001 |
| CA | 2598048 A1 | 5/2008 |

(Continued)

OTHER PUBLICATIONS

Extended European Search Report issued in corresponding European Application No. 19 20 2683 dated Apr. 3, 2020.

(Continued)

*Primary Examiner* — Phong Son H Dang
(74) *Attorney, Agent, or Firm* — Troutman Pepper Hamilton Sanders LLP

(57) ABSTRACT

Devices can generally include an implant having a braided section that can be implanted in a deployed state such that, in the deployed state, the braided section folds to form an outer occlusive sack extending across a neck of an aneurysm to engage a wall of the aneurysm from within a sac of the aneurysm and an inner occlusive sack forming a trough nested within the outer occlusive sack. The implant can be closed at one or more of the braid ends to define a substantially enclosed bowl-shaped volume.

14 Claims, 13 Drawing Sheets

(56) References Cited

U.S. PATENT DOCUMENTS

| | | | |
|---|---|---|---|
| 4,991,602 A | 2/1991 | Amplatz et al. | |
| 5,002,556 A | 3/1991 | Ishida et al. | |
| 5,025,060 A | 6/1991 | Yabuta et al. | |
| 5,065,772 A | 11/1991 | Cox, Jr. | |
| 5,067,489 A | 11/1991 | Lind | |
| 5,122,136 A | 6/1992 | Guglielmi et al. | |
| 5,192,301 A | 3/1993 | Kamiya et al. | |
| 5,261,916 A * | 11/1993 | Engelson | A61B 17/12022 606/108 |
| 5,304,195 A * | 4/1994 | Twyford, Jr. | A61B 17/12022 606/191 |
| 5,334,210 A | 8/1994 | Gianturco | |
| 5,350,397 A | 9/1994 | Palermo | |
| 5,423,829 A | 6/1995 | Pham et al. | |
| 5,624,449 A | 4/1997 | Pham et al. | |
| 5,645,558 A | 7/1997 | Horton | |
| 5,733,294 A | 3/1998 | Forber et al. | |
| 5,916,235 A | 6/1999 | Guglielmi | |
| 5,891,128 A | 7/1999 | Yen Chin et al. | |
| 5,928,260 A * | 7/1999 | Chin | A61B 17/12022 604/107 |
| 5,935,148 A | 8/1999 | Villar | |
| 5,941,249 A | 8/1999 | Maynard | |
| 5,951,599 A | 9/1999 | McCrory | |
| 5,964,797 A | 10/1999 | Ho | |
| 6,007,573 A | 12/1999 | Wallace et al. | |
| 6,024,756 A | 2/2000 | Pham | |
| 6,036,720 A | 3/2000 | Abrams | |
| 6,063,070 A | 5/2000 | Eder | |
| 6,063,100 A * | 5/2000 | Diaz | A61B 17/12022 606/191 |
| 6,063,104 A | 5/2000 | Villar | |
| 6,080,191 A | 6/2000 | Thaler | |
| 6,086,577 A | 7/2000 | Ken et al. | |
| 6,096,021 A | 8/2000 | Helm et al. | |
| 6,113,609 A | 9/2000 | Adams | |
| 6,123,714 A | 9/2000 | Gia et al. | |
| 6,168,615 B1 | 1/2001 | Ken | |
| 6,168,622 B1 | 1/2001 | Mazzocchi | |
| 6,193,708 B1 | 2/2001 | Ken et al. | |
| 6,221,086 B1 | 4/2001 | Forber | |
| 6,270,515 B1 | 8/2001 | Linden et al. | |
| 6,315,787 B1 | 11/2001 | Tsugita et al. | |
| 6,331,184 B1 * | 12/2001 | Abrams | A61B 17/12022 604/164.09 |
| 6,334,048 B1 | 12/2001 | Edvardsson et al. | |
| 6,346,117 B1 | 2/2002 | Greenhalgh | |
| 6,350,270 B1 | 2/2002 | Roue | |
| 6,375,606 B1 | 4/2002 | Garbaldi et al. | |
| 6,375,668 B1 * | 4/2002 | Gifford | A61B 17/12022 606/200 |
| 6,379,329 B1 * | 4/2002 | Naglreiter | A61B 17/12113 604/101.02 |
| 6,391,037 B1 | 5/2002 | Greenhalgh | |
| 6,419,686 B1 | 7/2002 | McLeod et al. | |
| 6,428,558 B1 * | 8/2002 | Jones | A61B 17/12022 606/151 |
| 6,454,780 B1 * | 9/2002 | Wallace | A61B 17/12022 606/151 |
| 6,463,317 B1 | 10/2002 | Kucharczyk et al. | |
| 6,506,204 B2 | 1/2003 | Mazzocchi | |
| 6,527,919 B1 | 3/2003 | Roth | |
| 6,547,804 B2 | 4/2003 | Porter et al. | |
| 6,551,303 B1 | 4/2003 | Van Tassel et al. | |
| 6,569,179 B2 | 5/2003 | Teoh | |
| 6,569,190 B2 | 5/2003 | Whalen, II et al. | |
| 6,572,628 B2 | 6/2003 | Dominguez | |
| 6,589,230 B2 | 7/2003 | Gia et al. | |
| 6,589,256 B2 | 7/2003 | Forber | |
| 6,605,102 B1 | 8/2003 | Mazzocchi et al. | |
| 6,620,152 B2 | 9/2003 | Guglielmi | |
| 6,669,719 B2 | 12/2003 | Wallace et al. | |
| 6,689,159 B2 | 2/2004 | Lau et al. | |
| 6,746,468 B1 | 6/2004 | Sepetka | |
| 6,780,196 B2 | 8/2004 | Chin et al. | |
| 6,802,851 B2 | 10/2004 | Jones | |
| 6,811,560 B2 | 11/2004 | Jones | |
| 6,833,003 B2 | 12/2004 | Jones et al. | |
| 6,846,316 B2 | 1/2005 | Abrams | |
| 6,849,081 B2 * | 2/2005 | Sepetka | A61B 17/12022 606/1 |
| 6,855,154 B2 | 2/2005 | Abdel-Gawwad | |
| 6,949,116 B2 | 9/2005 | Solymar et al. | |
| 6,964,657 B2 * | 11/2005 | Cragg | A61B 17/12022 604/508 |
| 6,964,671 B2 | 11/2005 | Cheng | |
| 6,994,711 B2 * | 2/2006 | Hieshima | A61B 17/12022 606/108 |
| 7,044,134 B2 | 5/2006 | Khairkhahan et al. | |
| 7,083,632 B2 | 8/2006 | Avellanet | |
| 7,093,527 B2 | 8/2006 | Rapaport et al. | |
| 7,128,736 B1 | 10/2006 | Abrams et al. | |
| 7,152,605 B2 | 12/2006 | Khairkhahan et al. | |
| 7,153,323 B1 | 12/2006 | Teoh | |
| 7,195,636 B2 | 3/2007 | Avellanet et al. | |
| 7,229,454 B2 | 6/2007 | Tran et al. | |
| 7,229,461 B2 | 6/2007 | Chin et al. | |
| 7,309,345 B2 | 12/2007 | Wallace | |
| 7,371,249 B2 | 5/2008 | Douk et al. | |
| 7,410,482 B2 | 8/2008 | Murphy et al. | |
| 7,572,288 B2 | 8/2009 | Cox | |
| 7,597,704 B2 | 10/2009 | Frazier et al. | |
| 7,608,088 B2 | 10/2009 | Jones | |
| 7,695,488 B2 * | 4/2010 | Berenstein | A61B 17/12177 606/194 |
| 7,713,264 B2 | 5/2010 | Murphy | |
| 7,744,652 B2 | 6/2010 | Morsi | |
| 7,892,248 B2 | 2/2011 | Tran et al. | |
| 7,985,238 B2 * | 7/2011 | Balgobin | A61B 17/12113 606/200 |
| RE42,758 E | 9/2011 | Ken et al. | |
| 8,016,852 B2 | 9/2011 | Ho | |
| 8,021,416 B2 | 9/2011 | Abrams | |
| 8,025,668 B2 | 9/2011 | McCartney | |
| 8,034,061 B2 | 10/2011 | Amplatz et al. | |
| 8,048,145 B2 | 11/2011 | Evans et al. | |
| 8,062,325 B2 * | 11/2011 | Mitelberg | A61F 2/95 606/200 |
| 8,075,585 B2 | 12/2011 | Lee et al. | |
| 8,142,456 B2 | 3/2012 | Rosqueta et al. | |
| 8,221,483 B2 | 7/2012 | Ford et al. | |
| 8,261,648 B1 | 9/2012 | Marchand et al. | |
| 8,267,923 B2 | 9/2012 | Murphy | |
| 8,361,106 B2 | 1/2013 | Solar et al. | |
| 8,361,138 B2 | 1/2013 | Adams | |
| 8,372,114 B2 | 2/2013 | Hines | |
| 8,398,671 B2 | 3/2013 | Chen | |
| 8,430,012 B1 | 4/2013 | Marchand | |
| 8,454,633 B2 | 6/2013 | Amplatz et al. | |
| 8,523,897 B2 | 9/2013 | van der Burg et al. | |
| 8,523,902 B2 * | 9/2013 | Heaven | A61B 17/0401 606/232 |
| 8,551,132 B2 * | 10/2013 | Eskridge | A61B 17/122 606/191 |
| 8,777,974 B2 | 7/2014 | Amplatz et al. | |
| 8,900,304 B1 * | 12/2014 | Alobaid | A61B 17/7097 623/17.12 |
| 8,974,512 B2 | 3/2015 | Aboytes et al. | |
| 8,992,568 B2 | 3/2015 | Duggal et al. | |
| 8,998,947 B2 | 4/2015 | Aboytes et al. | |
| 9,055,948 B2 | 6/2015 | Jaeger et al. | |
| 9,107,670 B2 | 8/2015 | Hannes | |
| 9,161,758 B2 * | 10/2015 | Figulla | A61B 17/12022 |
| 9,232,992 B2 | 1/2016 | Heidner et al. | |
| 9,259,337 B2 * | 2/2016 | Cox | A61F 2/86 |
| 9,314,326 B2 | 4/2016 | Wallace et al. | |
| 9,351,715 B2 | 5/2016 | Mach | |
| 9,414,842 B2 | 8/2016 | Glimsdale et al. | |
| 9,526,813 B2 | 12/2016 | Cohn et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |

(56) References Cited

U.S. PATENT DOCUMENTS

| | | | |
|---|---|---|---|
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 * | 2/2017 | Beckham | A61B 17/12113 |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Helsel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Peterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 * | 11/2018 | Griffin | A61B 17/12031 |
| 10,307,148 B2 | 6/2019 | Helsel et al. |
| 10,327,781 B2 | 6/2019 | Divino et al. |
| 10,342,546 B2 | 7/2019 | Sepetka et al. |
| 10,716,573 B2 * | 7/2020 | Connor | A61B 17/12163 |
| 2002/0068974 A1 * | 6/2002 | Kuslich | A61F 2/441 |
| | | | 623/17.11 |
| 2002/0082638 A1 | 6/2002 | Porter et al. |
| 2002/0143349 A1 | 10/2002 | Gifford, III et al. |
| 2002/0147497 A1 * | 10/2002 | Belef | A61F 2/4611 |
| | | | 623/17.12 |
| 2002/0188314 A1 | 12/2002 | Anderson et al. |
| 2003/0028209 A1 * | 2/2003 | Teoh | A61B 17/12172 |
| | | | 606/191 |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 * | 10/2003 | Wallace | A61B 17/12172 |
| | | | 606/200 |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | VanTassel et al. |
| 2004/0133222 A1 | 7/2004 | Tran et al. |
| 2004/0153120 A1 | 8/2004 | Seifert et al. |
| 2004/0210297 A1 * | 10/2004 | Lin | A61B 17/7097 |
| | | | 623/1.11 |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 * | 3/2006 | Guterman | A61B 17/12172 |
| | | | 623/1.3 |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 * | 7/2006 | Suddaby | A61B 17/12022 |
| | | | 606/213 |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 * | 7/2007 | Euteneuer | A61M 25/09 |
| | | | 600/585 |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 * | 5/2008 | Fransen | A61B 17/7097 |
| | | | 606/92 |
| 2008/0281350 A1 * | 11/2008 | Sepetka | A61B 17/12172 |
| | | | 606/200 |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 * | 9/2009 | Griffin | A61M 25/0068 |
| | | | 604/526 |
| 2009/0281557 A1 | 11/2009 | Sander et al. |
| 2009/0287291 A1 * | 11/2009 | Becking | A61B 17/12118 |
| | | | 623/1.11 |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 * | 3/2010 | Veznedaroglu | A61B 17/12022 |
| | | | 606/194 |
| 2010/0168781 A1 | 7/2010 | Berenstein |
| 2010/0324649 A1 | 12/2010 | Mattsson et al. |
| 2011/0046658 A1 | 2/2011 | Connor et al. |
| 2011/0054519 A1 | 3/2011 | Neuss |
| 2011/0112588 A1 * | 5/2011 | Linderman | A61B 17/8855 |
| | | | 606/86 R |
| 2011/0137317 A1 * | 6/2011 | O'Halloran | A61B 17/8855 |
| | | | 606/92 |
| 2011/0152993 A1 * | 6/2011 | Marchand | A61B 17/12172 |
| | | | 623/1.2 |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |

(56) References Cited

U.S. PATENT DOCUMENTS

| | | | |
|---|---|---|---|
| 2012/0165732 A1* | 6/2012 | Muller | A61B 17/8855 604/99.01 |
| 2012/0191123 A1* | 7/2012 | Brister | A61M 25/10186 606/191 |
| 2012/0283768 A1 | 11/2012 | Cox et al. | |
| 2012/0310270 A1 | 12/2012 | Murphy | |
| 2012/0323267 A1* | 12/2012 | Ren | A61B 17/12172 606/191 |
| 2012/0330341 A1 | 12/2012 | Becking et al. | |
| 2013/0035665 A1 | 2/2013 | Chu | |
| 2013/0035712 A1 | 2/2013 | Theobald et al. | |
| 2013/0066357 A1 | 3/2013 | Aboytes et al. | |
| 2013/0079864 A1 | 3/2013 | Boden | |
| 2013/0110066 A1 | 5/2013 | Sharma et al. | |
| 2013/0204351 A1 | 8/2013 | Cox et al. | |
| 2013/0211495 A1 | 8/2013 | Halden et al. | |
| 2013/0261658 A1* | 10/2013 | Lorenzo | A61B 17/1214 606/200 |
| 2013/0261730 A1 | 10/2013 | Bose et al. | |
| 2013/0345738 A1 | 12/2013 | Eskridge | |
| 2014/0005714 A1 | 1/2014 | Quick et al. | |
| 2014/0012307 A1 | 1/2014 | Franano et al. | |
| 2014/0012363 A1 | 1/2014 | Franano et al. | |
| 2014/0018838 A1 | 1/2014 | Franano et al. | |
| 2014/0135812 A1 | 5/2014 | Divino et al. | |
| 2014/0200607 A1 | 7/2014 | Sepetka et al. | |
| 2014/0257360 A1 | 9/2014 | Keillor | |
| 2014/0277013 A1 | 9/2014 | Sepetka et al. | |
| 2015/0057703 A1 | 2/2015 | Ryan et al. | |
| 2015/0209050 A1 | 7/2015 | Aboytes et al. | |
| 2015/0272589 A1 | 10/2015 | Lorenzo | |
| 2015/0313605 A1* | 11/2015 | Griffin | A61B 90/39 606/200 |
| 2015/0342613 A1 | 12/2015 | Aboytes et al. | |
| 2015/0374483 A1 | 12/2015 | Janardhan et al. | |
| 2016/0022445 A1 | 1/2016 | Ruvalcaba et al. | |
| 2016/0030050 A1 | 2/2016 | Franano et al. | |
| 2016/0192912 A1 | 7/2016 | Kassab et al. | |
| 2016/0249934 A1* | 9/2016 | Hewitt | A61B 17/12177 606/200 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu | |
| 2017/0027640 A1 | 2/2017 | Kunis et al. | |
| 2017/0027692 A1 | 2/2017 | Bonhoeffer | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079661 A1 | 3/2017 | Bardsley et al. | |
| 2017/0079662 A1 | 3/2017 | Rhee et al. | |
| 2017/0079671 A1 | 3/2017 | Morero | |
| 2017/0079680 A1 | 3/2017 | Bowman | |
| 2017/0079717 A1 | 3/2017 | Walsh et al. | |
| 2017/0079766 A1 | 3/2017 | Wang | |
| 2017/0079767 A1 | 3/2017 | Leon-Yip | |
| 2017/0079812 A1 | 3/2017 | Lam et al. | |
| 2017/0079817 A1 | 3/2017 | Sepetka | |
| 2017/0079819 A1 | 3/2017 | Pung et al. | |
| 2017/0079820 A1 | 3/2017 | Lam et al. | |
| 2017/0086851 A1 | 3/2017 | Wallace | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein | |
| 2017/0165454 A1 | 6/2017 | Tuohy | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0114350 A1 | 8/2017 | Shimizu et al. | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh | |
| 2017/0303942 A1 | 10/2017 | Greenhalgh et al. | |
| 2017/0303947 A1 | 10/2017 | Greenhalgh | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman | |
| 2017/0333228 A1 | 11/2017 | Orth et al. | |
| 2017/0333236 A1 | 11/2017 | Greenan | |
| 2017/0333678 A1 | 11/2017 | Bowman | |
| 2017/0340333 A1 | 11/2017 | Badruddin et al. | |
| 2017/0340383 A1 | 11/2017 | Bloom et al. | |
| 2017/0348014 A1 | 12/2017 | Wallace | |
| 2017/0348514 A1 | 12/2017 | Guyon et al. | |
| 2018/0140305 A1* | 5/2018 | Connor | A61F 2/90 |
| 2018/0242929 A1* | 8/2018 | Lorenzo | A61B 17/12031 |
| 2018/0303531 A1 | 10/2018 | Sanders et al. | |
| 2018/0338767 A1 | 11/2018 | Dasnurkar et al. | |
| 2019/0008522 A1 | 1/2019 | Lorenzo | |
| 2019/0110796 A1 | 4/2019 | Jayaraman | |
| 2019/0192162 A1 | 6/2019 | Lorenzo | |
| 2019/0192167 A1 | 6/2019 | Lorenzo | |
| 2019/0192168 A1 | 6/2019 | Lorenzo | |
| 2019/0223878 A1* | 7/2019 | Lorenzo | A61B 17/12031 |
| 2019/0223879 A1 | 7/2019 | Jayaraman | |
| 2019/0328398 A1 | 10/2019 | Lorenzo | |
| 2019/0365385 A1 | 12/2019 | Gorochow et al. | |
| 2020/0268365 A1 | 8/2020 | Hebert et al. | |

FOREIGN PATENT DOCUMENTS

| | | |
|---|---|---|
| CA | 2 431 594 A1 | 9/2009 |
| CN | 204 683 687 U | 10/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |

(56) References Cited

FOREIGN PATENT DOCUMENTS

| | | |
|---|---|---|
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2 647 343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 2005020822 A1 | 3/2005 |
| WO | WO 2005074814 A2 | 8/2005 |
| WO | 2005117718 A1 | 12/2005 |
| WO | WO 2006034149 A2 | 3/2006 |
| WO | 2006/052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2014029835 A1 | 2/2014 |
| WO | WO 2014110589 A1 | 7/2014 |
| WO | WO 2014137467 A1 | 9/2014 |
| WO | WO 2015073704 A1 | 5/2015 |
| WO | 2015160721 A1 | 10/2015 |
| WO | 2015171268 A2 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2018051187 A1 | 3/2018 |
| WO | WO 2012/034135 A1 | 3/2021 |

OTHER PUBLICATIONS

Extended European Search Report dated May 2, 2019 in corresponding European Application No. 18214052.5.
Extended European Search Report issued in corresponding European Patent Application No. 19 21 5277 dated May 12, 2020.
Altes et al., Creation of Saccular Aneurysms in the Rabbit: A Model Suitable for Testing Endovascular Devices. AJR 2000; 174: 349-354.
Schaffer, Advanced Materials & Processes, Oct. 2002, pp. 51-54.

* cited by examiner

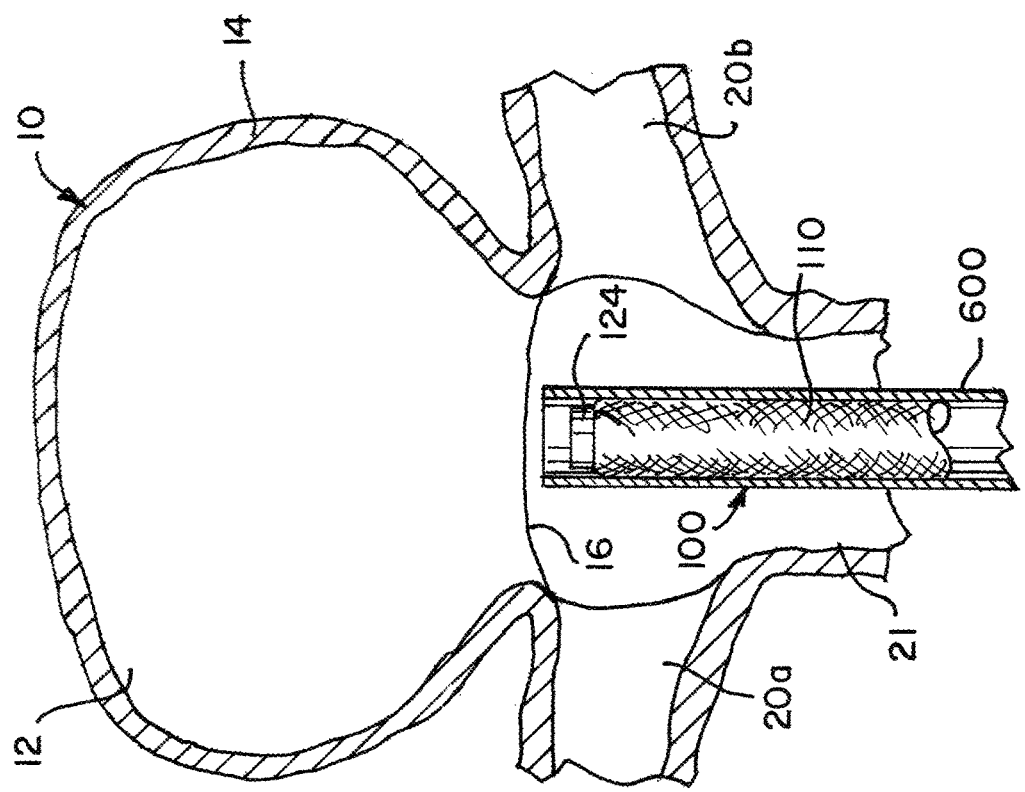
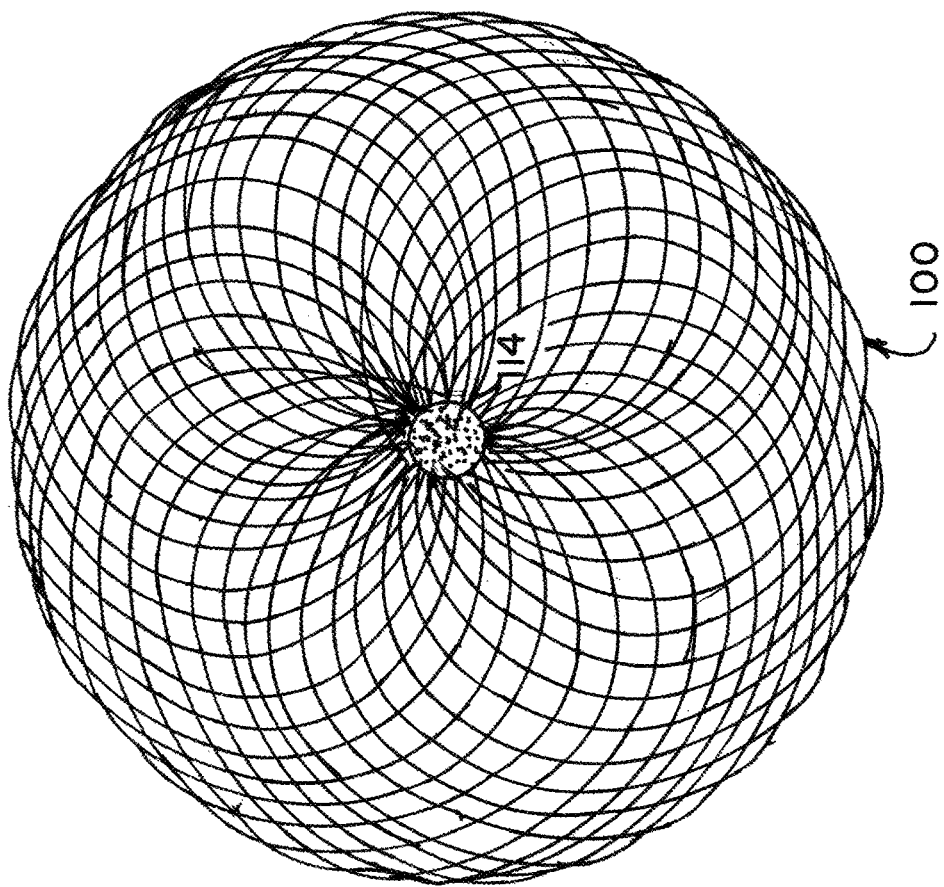

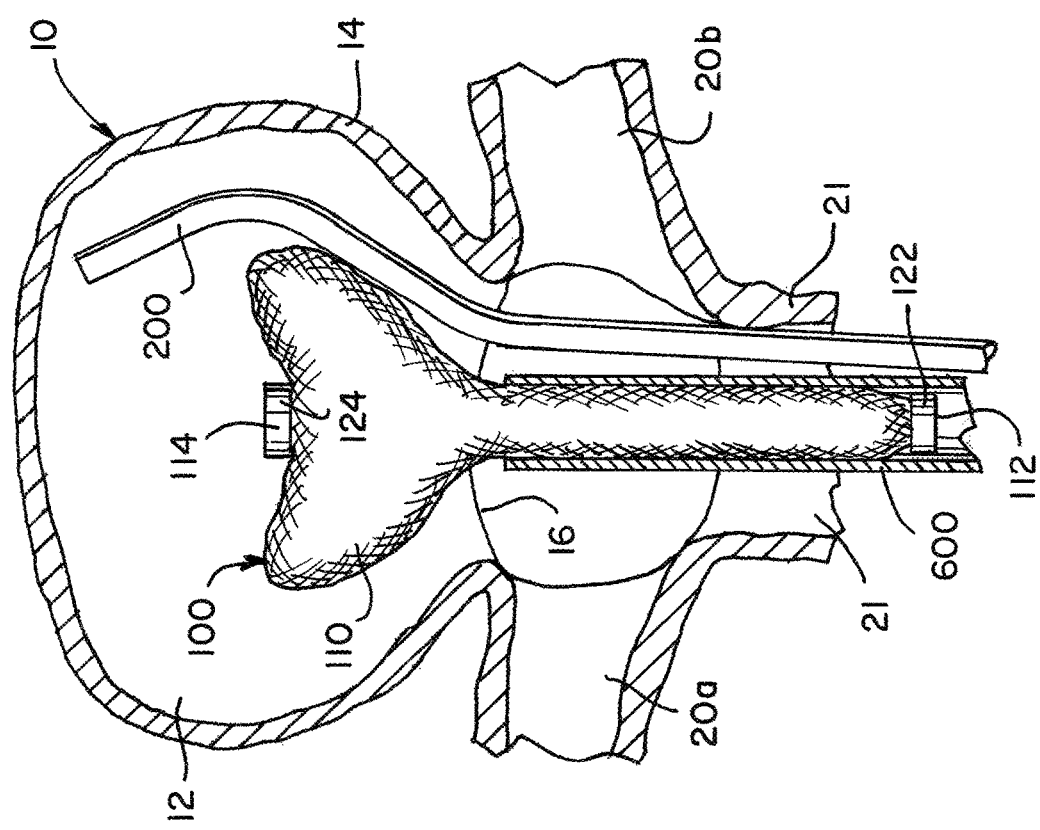
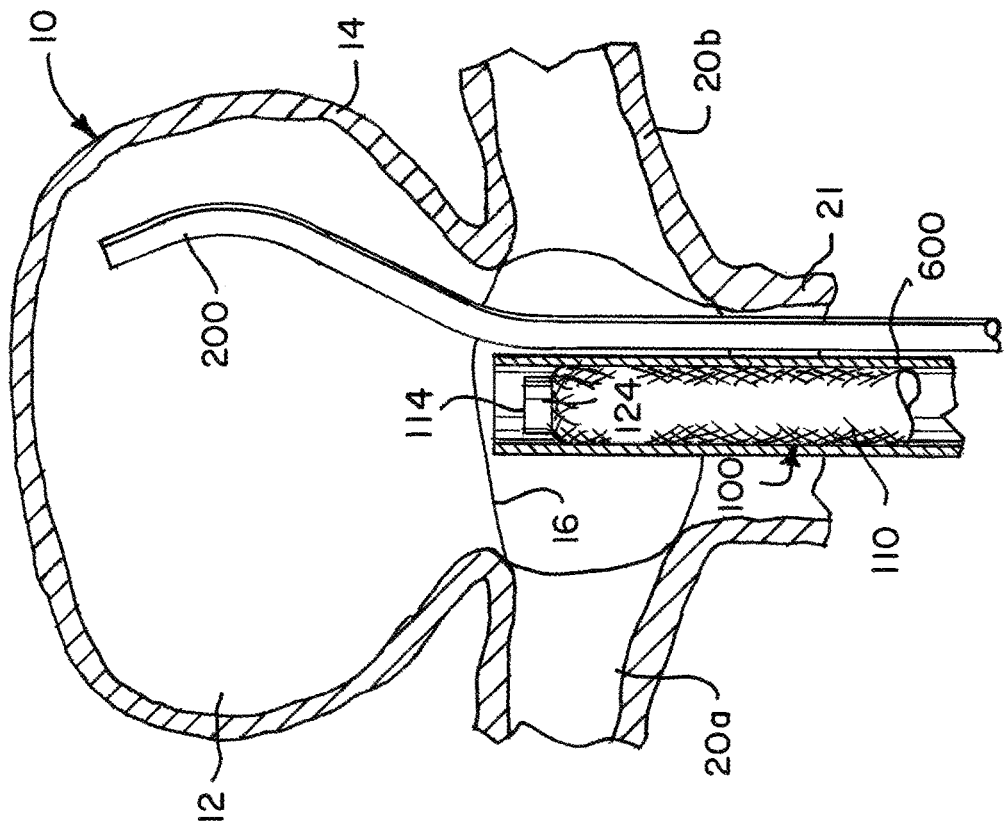

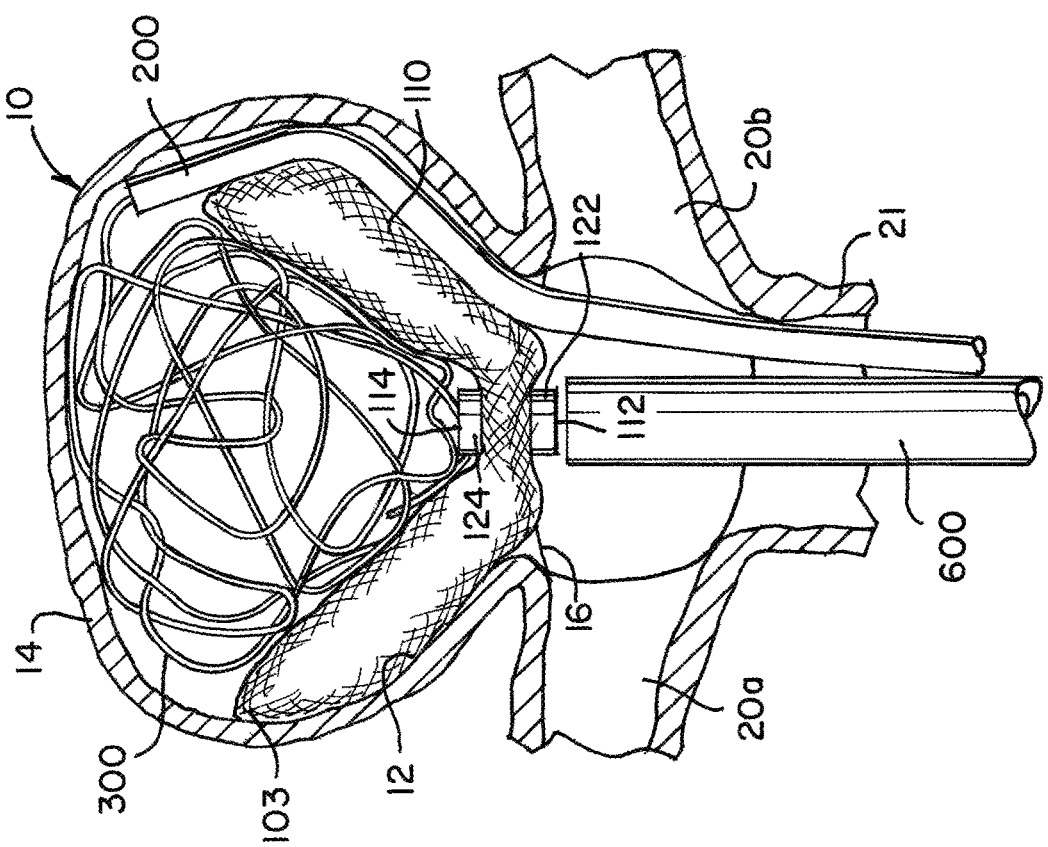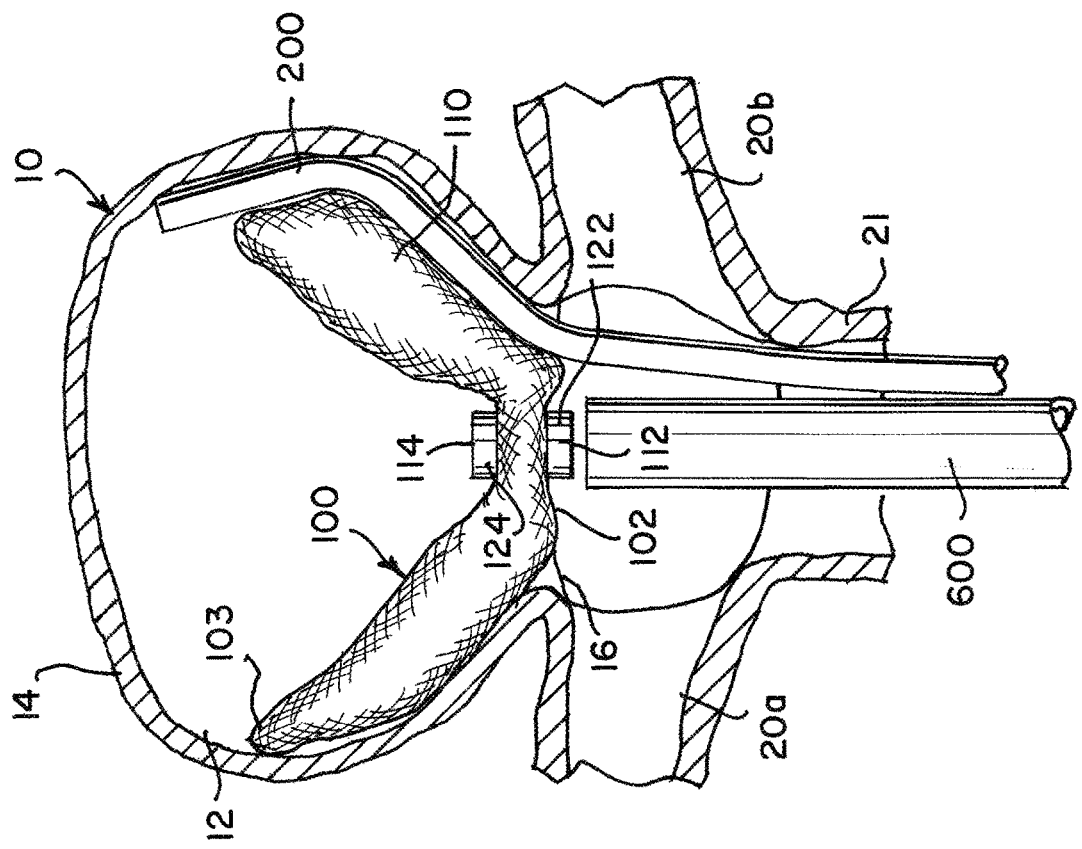

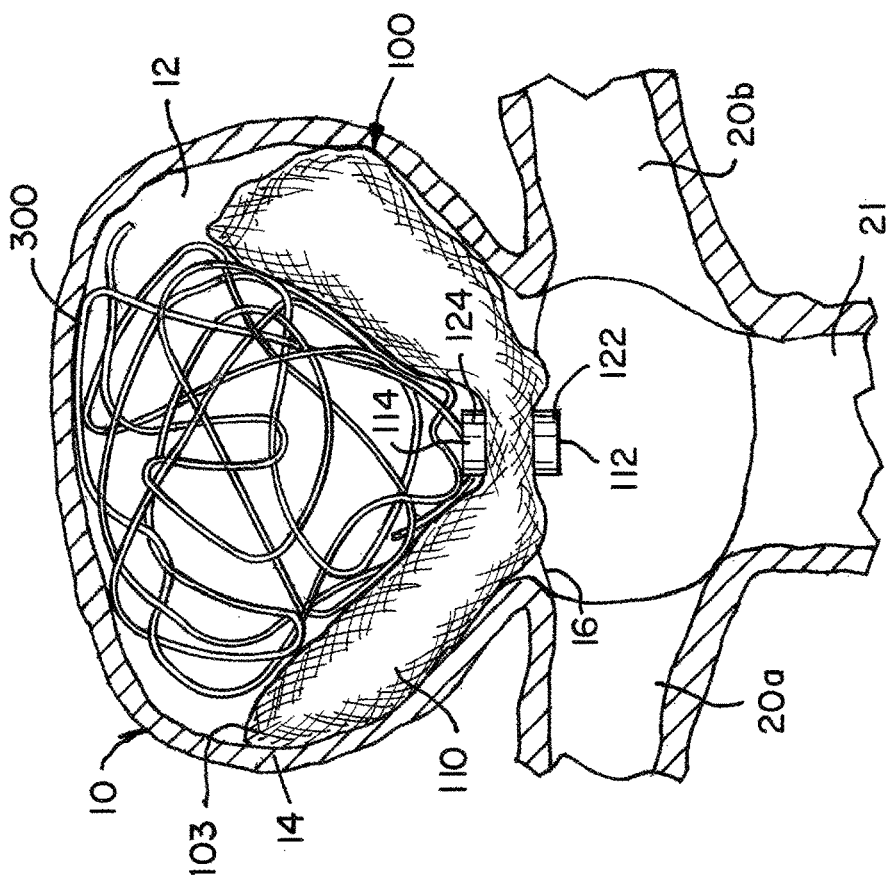
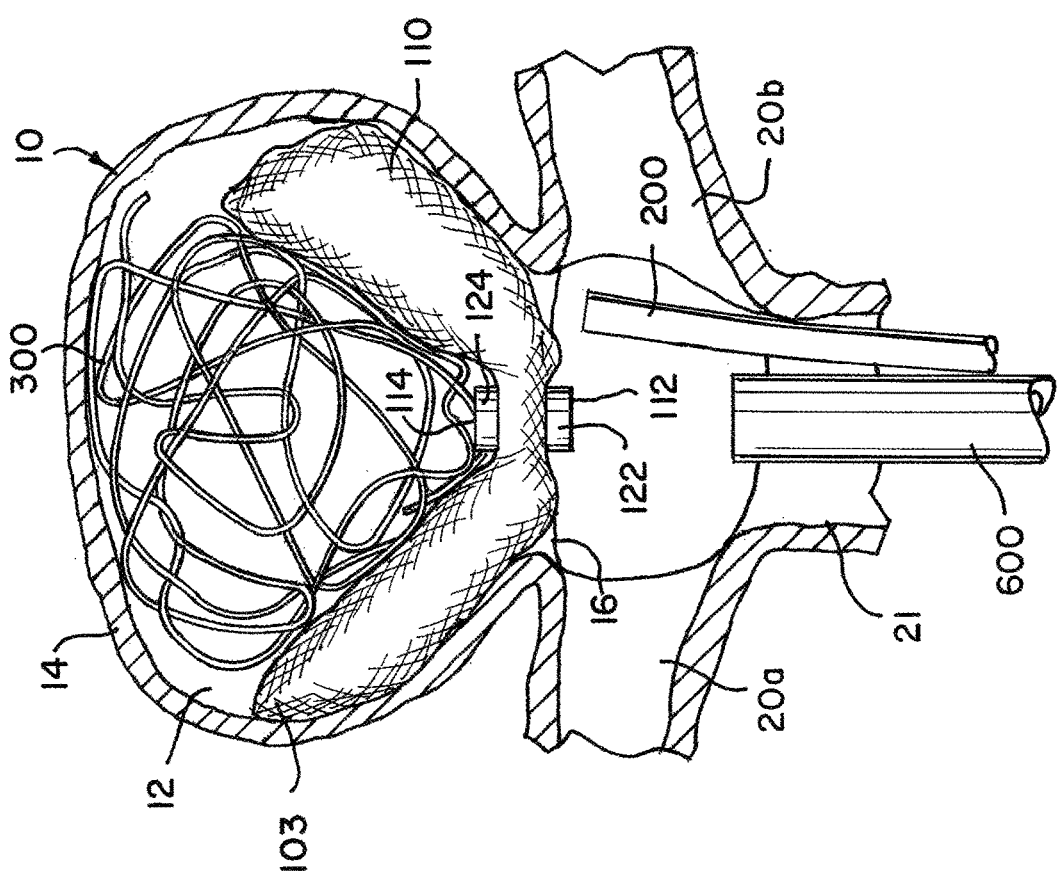

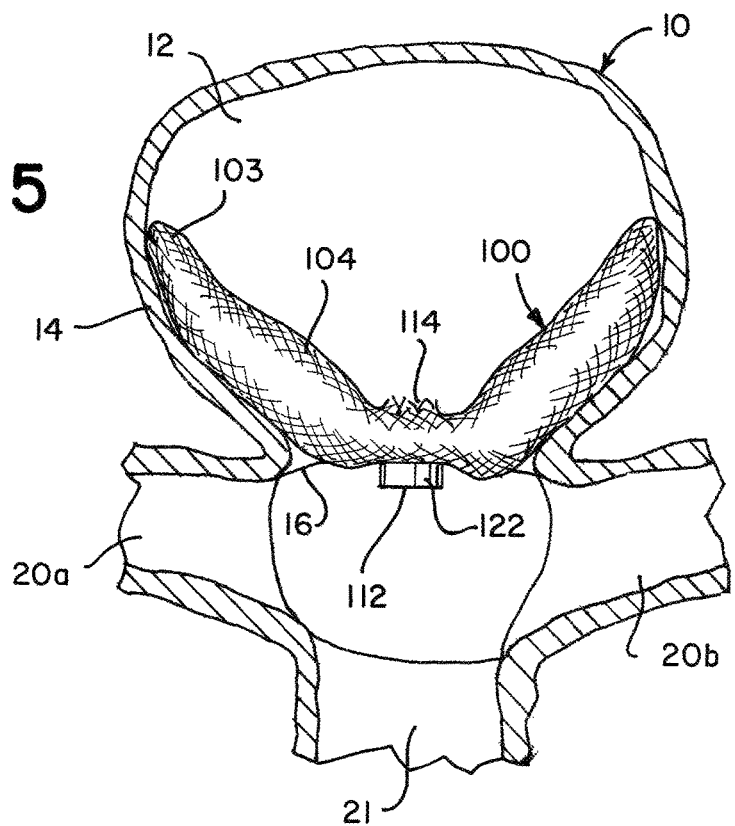
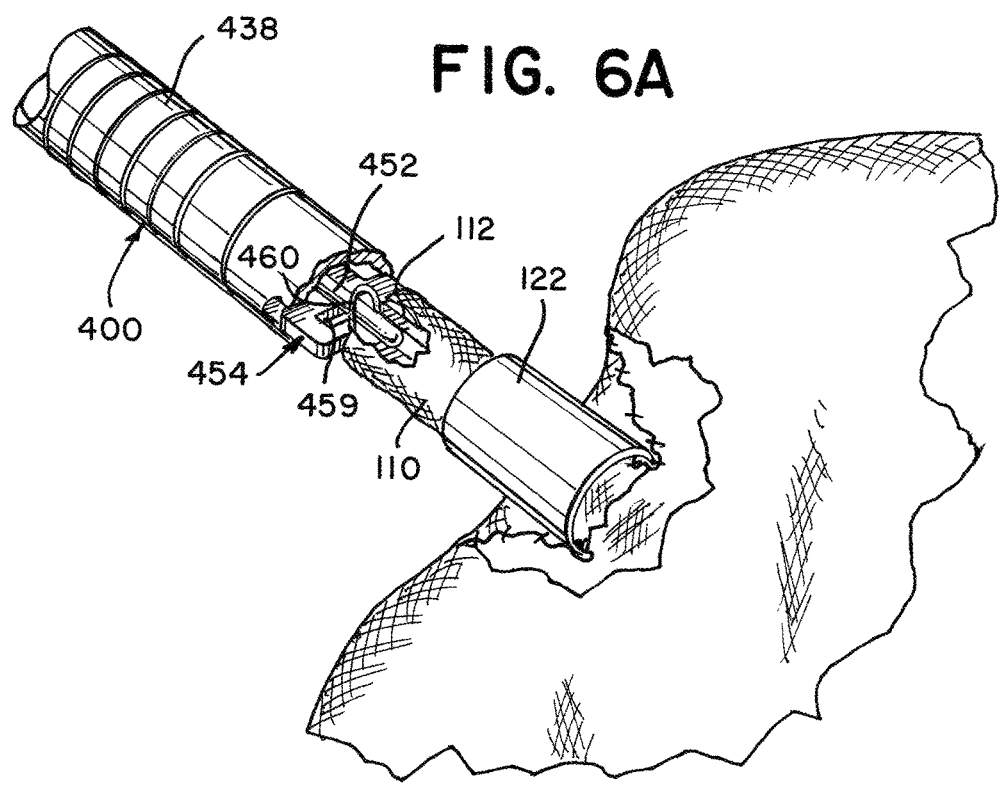

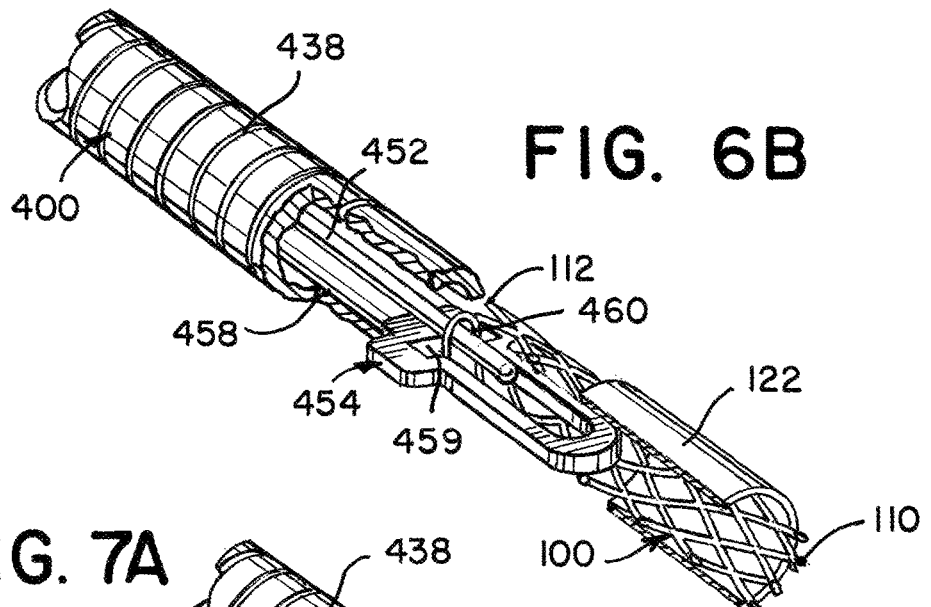
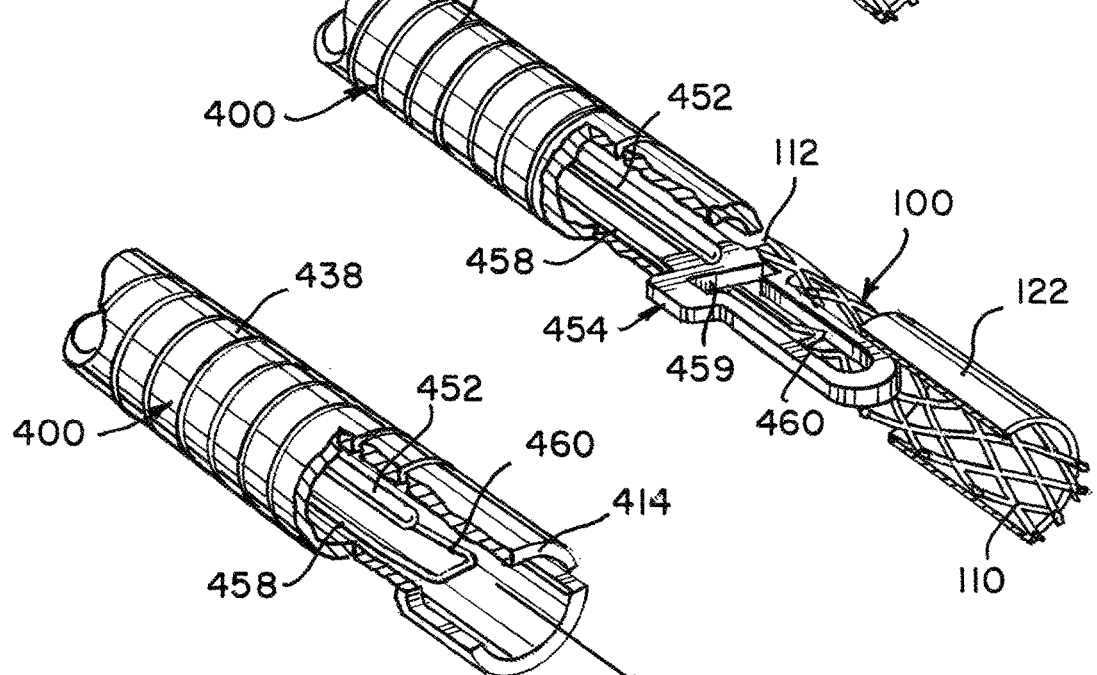
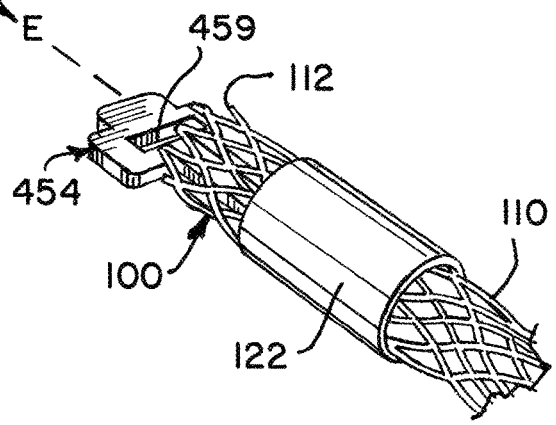

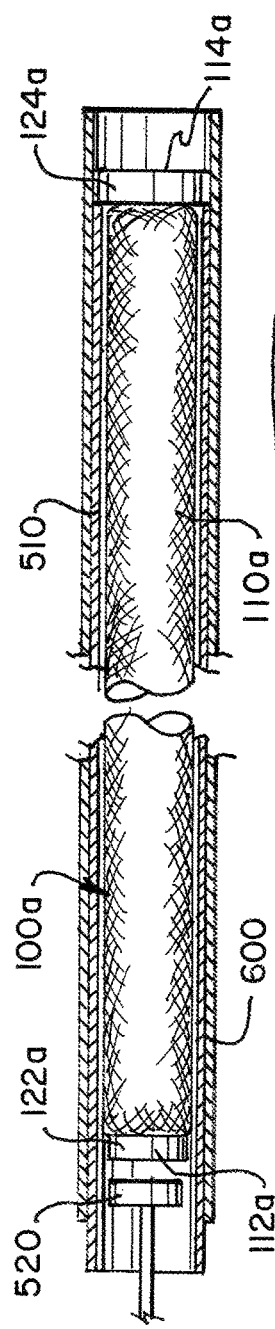
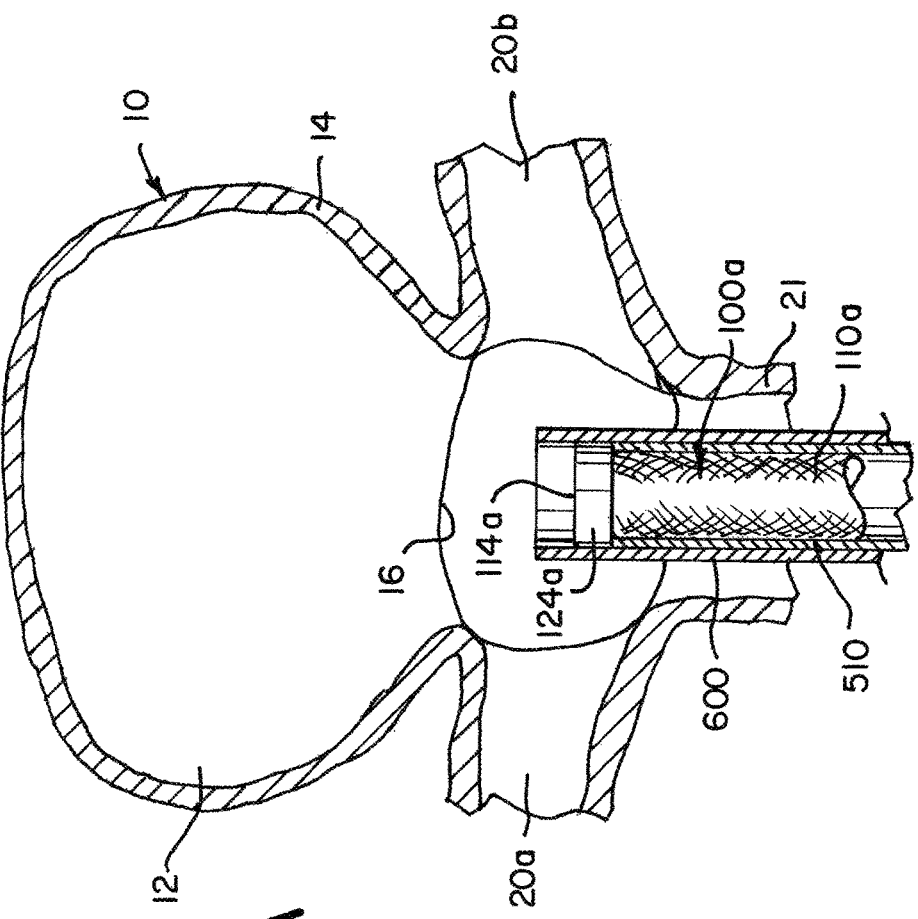

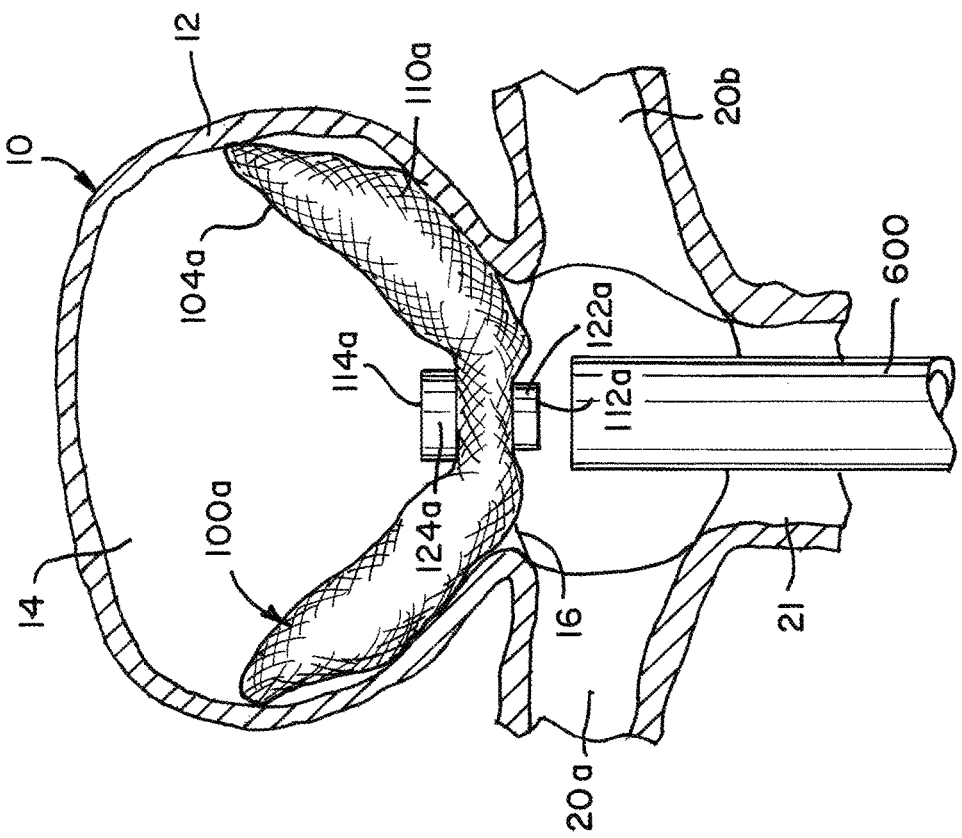
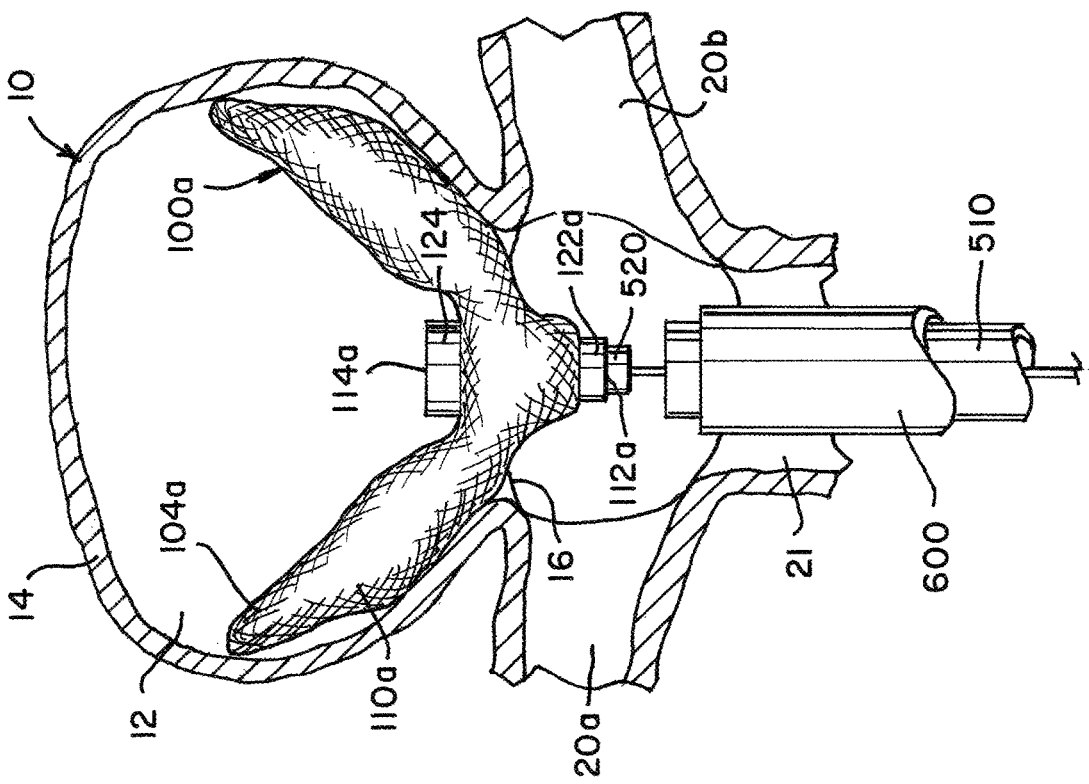

FOLDED ANEURYSM TREATMENT DEVICE AND DELIVERY METHOD

FIELD OF THE INVENTION

The present invention generally relates to medical instruments, and more particularly, to implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Such solutions, however can result in the interior walls of the aneurysm being subjected to flow of blood and related blood pressure even after treatment, and the aneurysm can rupture as a result.

Current alternatives to endovascular or other surgical approaches can include occlusion devices that either fill the sac of the aneurysm with embolic material or treating the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current occlusion devices typically utilize multiple embolic coils to either fill the sac or treat the entrance. In either treatment, obtaining an embolic coil packing density sufficient to either occlude the aneurysm neck or fill the aneurysm sac is difficult and time consuming. Further, aneurysm morphology (e.g. wide neck, bifurcation, etc.) can required ancillary devices such a stents or balloons to support the coil mass and obtain the desired packing density.

Naturally formed thrombotic masses formed by treating the entrance of the aneurysm with embolic coils can improve healing compared to aneurysm masses packed with embolic coils by reducing possible distention from arterial walls and permitting reintegration into the original parent vessel shape along the neck plane. However, embolic coils delivered to the neck of the aneurysm can potentially have the adverse effect of impeding the flow of blood in the adjoining blood vessel; at the same time, if the entrance is insufficiently packed, blood flow can persist into the aneurysm. Properly implanting embolic coils is therefore challenging, and once implanted, the coils cannot easily be retracted or repositioned.

Furthermore, embolic coils do not always effectively treat aneurysms as aneurysms treated with multiple coils often reanalyze or compact because of poor coiling, lack of coverage across the aneurysm neck, because of flow, or even aneurysm size.

An example alternative occlusion device is described in U.S. Pat. No. 8,998,947. However, this approach relies upon the use of embolic coils or mimics the coil approach and therefore suffers many of the limitations of embolic coil approaches such as difficulty achieving a safe packing density and inability to reposition once implanted.

It is therefore desirable to have a device which easily, accurately, and safely occludes a neck of an aneurysm or other arterio-venous malformation in a parent vessel without blocking flow into perforator vessels communicating with the parent vessel.

SUMMARY

Disclosed herein are various exemplary devices for occluding an aneurysm that can address the above needs. The devices can generally include an implant having a braided section that can be implanted in a deployed state such that, in the deployed state, the braided section folds to form an outer occlusive sack extending across a neck of an aneurysm to engage a wall of the aneurysm from within a sac of the aneurysm and an inner occlusive sack forming a trough nested within the outer occlusive sack. The implant can be closed at one or more of the braid ends to define a substantially enclosed bowl-shaped volume.

An example device for occluding an aneurysm can include an implant that is movable from a collapsed state to a deployed state. The implant can have a proximal end, a distal end, and a braided segment forming a substantially continuous braided structure between the proximal end and the distal end. In the deployed state, the implant can have an outer occlusive sack, an inner occlusive sack, and a fold between the outer occlusive sack and the inner occlusive sack. The outer occlusive sack can extend from the proximal end of the implant and can occlude an aneurysm neck. The inner occlusive sack can extend from the distal end of the implant and form a trough within the outer occlusive sack.

The braided segment can have a first portion that is capable of self-expanding to form the outer occlusive sack and a second portion that is capable of self-inverting to form the inner occlusive sack.

In the deployed state, the outer occlusive sack can extend to an aneurysm wall to provide a force against the aneurysm wall. In the deployed state, opposition of the outer occlusive sack to the aneurysm wall can be sufficient to maintain the position of the implant within the aneurysm.

The device can further include an embolic filler that is implantable in a sac of the aneurysm. In the deployed state, the implant can inhibit the embolic filler from exiting the sac, and the embolic filler can provide a force to appose the implant to the aneurysm wall.

In the collapsed state, the implant can be sized to be delivered to the aneurysm through a microcatheter.

Either the proximal end or the distal end, or both, can be closed. The device can include end closure mechanisms positioned at one or both ends. The end closure mechanisms can be bands or end caps.

The braided segment can be made of a memory shape material having a first, predetermined shape and a second, deformed shape. The braided segment can be in the second, deformed shape when the implant is in the collapsed state and can move to a third, deployed shape when the implant is in the deployed state. The third, deployed shape can be based at least in part on the predetermined shape and the shape of the aneurysm wall.

In the deployed state, the outer occlusive sack can seal the aneurysm neck to deflect, divert, and/or slow a flow of blood into the aneurysm. In the deployed state, the implant can define a substantially enclosed volume. In the deployed state, the distal end and the proximal end of the implant can each be positioned along an axis approximately perpendicular to the aneurysm neck and approximate a center of the aneurysm neck.

The implant can be implantable in an aneurysm positioned adjacent bifurcated blood vessel branches, and the implant can be delivered to the aneurysm through a stem branch feeding the bifurcated blood vessel branches.

In another example, an implant for treating an aneurysm can have a braided mesh that is movable to an implanted configuration such that the braided mesh has a substantially contiguous surface defining a substantially enclosed, bowl-shaped volume in the implanted configuration. The braided mesh can be movable from a substantially tubular configuration having a first send and a second end to the implanted configuration, and when in the implanted configuration, the first end and the second end can each be positioned approximate a center of the bowl-shaped volume, and a fold in the braided mesh can define an annular ridge of the bowl-shaped volume.

An example method of occluding an aneurysm can include positioning an expandable braid in a collapsed state within a microcatheter, distally sliding the braid through the microcatheter towards the aneurysm, expelling a first portion of the braid that includes a distal end of the braid from the microcatheter into an aneurysm sac, expanding the first portion of the braid, expelling a second portion of the braid including a proximal end of the braid from the microcatheter into the aneurysm sac, expanding the second portion of the braid to occlude a neck of the aneurysm and to form an outer occlusive sack, and inverting the first portion of the braid to form an inner occlusive sack nested within the outer occlusive sack. The second portion of the braid can be expanded to form the outer occlusive sack such that a proximal end of the braid is positioned near a center of the neck of the aneurysm and the second portion of the braid extends radially from the proximal end to form the outer occlusive sack. The braid can be self-expanding.

The method can include positioning a distal end of a second catheter for delivering an embolic implant such that the distal end is positioned within the aneurysm sac. The step of expanding the second portion of the braid can include confining the second catheter between the second portion of the braid and a first portion of a wall of the aneurysm.

The method can include delivering the embolic implant to the aneurysm through the second catheter, implanting the embolic implant in the aneurysm sac, and providing a force from the embolic implant to appose at least a portion of the braid to a second portion of the wall of the aneurysm.

The method can include providing a force between the outer occlusive sack and an aneurysm wall sufficient to maintain an implanted position of the braid within the aneurysm.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1C is an illustration of an exemplary implant in a deployed state as viewed from the distal end according to aspects of the present invention;

FIGS. 3A to 3F are illustrations of an implantation sequence of an exemplary implant according to aspects of the present invention;

FIGS. 4A to 4G are illustrations of another implantation sequence of an exemplary implant according to aspects of the present invention;

FIG. 5 is an illustration of an exemplary implant absent a distal closure member implanted in a deployed state according to aspects of the present invention;

FIG. 6A is a perspective schematic view showing an exemplary delivery system for use with an example implant according aspects of the present invention;

FIG. 6B is a perspective schematic view of FIG. 6A but with partial cross-section of the delivery system and the implant according aspects of the present invention;

FIG. 7A is a perspective schematic view of FIGS. 6A-6B being deployed with partial cross-section of the delivery system and the implant according aspects of the present invention;

FIG. 7B is a perspective schematic view of FIGS. 6A-6B deployed with the exemplary delivery system detached from the implant according aspects of the present invention;

FIG. 8 is an illustration of another exemplary device having an implant in a collapsed state according to aspects of the present invention;

FIGS. 9A to 9C are illustrations of an exemplary implantation sequence of the exemplary device of FIG. 8 according to aspects of the present invention;

DETAILED DESCRIPTION

In general, example devices described herein can include an implant having a flexible body expandable from a collapsed state in which the implant is shaped to be delivered through a microcatheter to an aneurysm treatment site to a deployed state in which the implant shaped to occlude an aneurysm from within an aneurysm sac. In the deployed state, the implant can generally have a bowl shape having an inner occlusive sack nested within an outer occlusive sack such that the outer occlusive sack and the inner occlusive sack are separated by a fold in the flexible body of the implant.

Figure 1A:
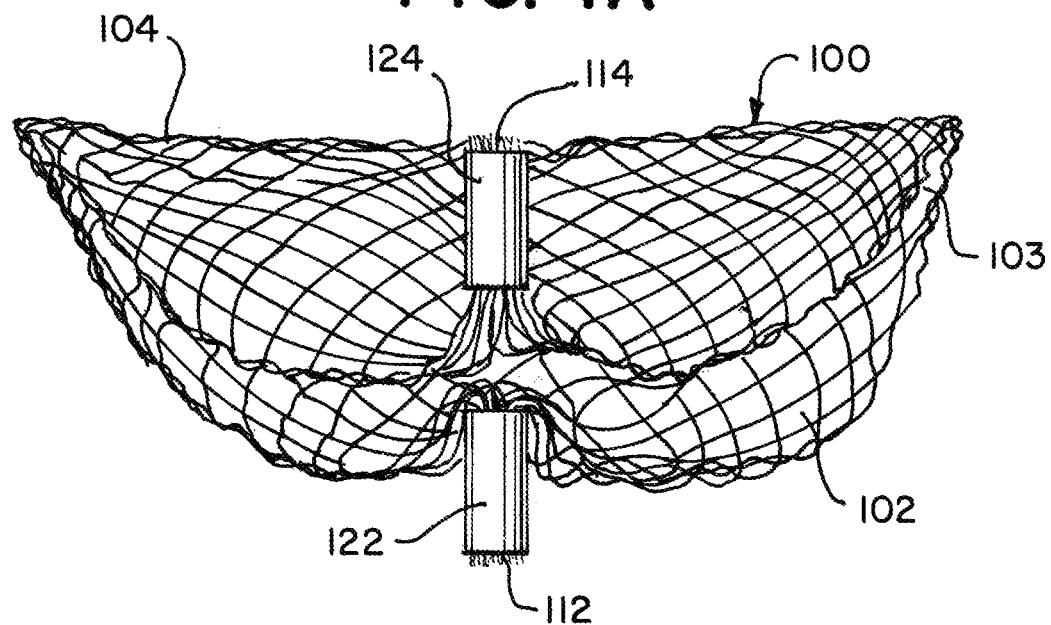
FIGS. 1A to 1B are illustrations of cross-sectioned exemplary implants in a deployed state according to aspects of the present invention.
Figure 1B:
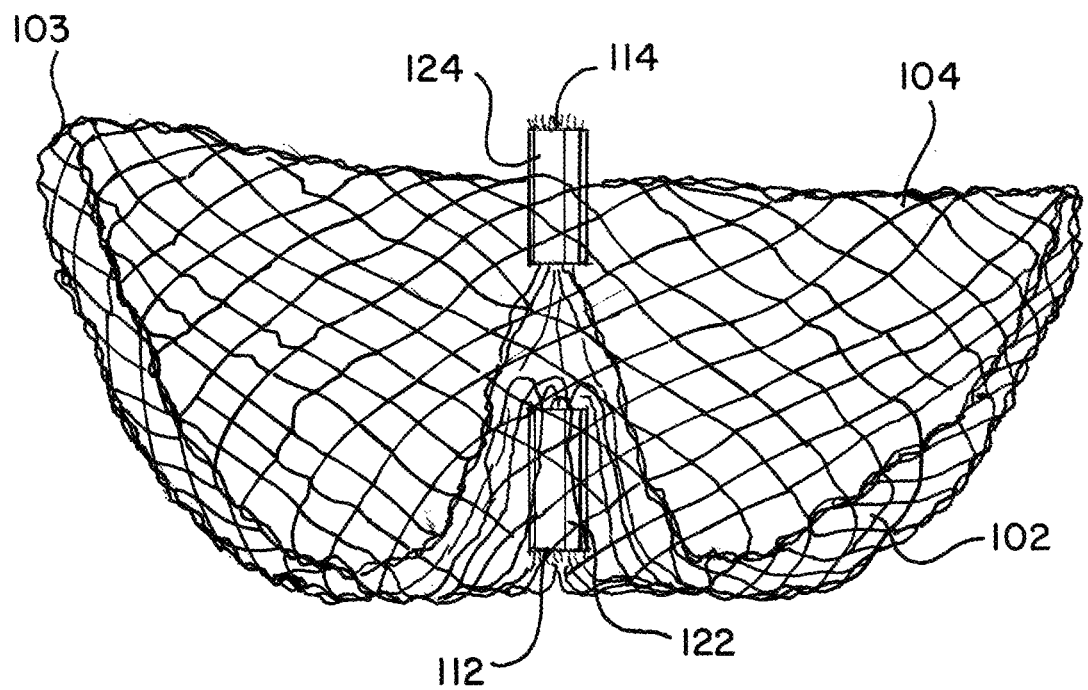

FIGS. 1A and 1B depict side views of a cross sectioned example implants in a deployed state. As illustrated, an implant 100 can have a braided mesh flexible body. The mesh can fold to define an inner occlusive sack 104 and an outer occlusive sack 102 separated by a fold 103. The implant 100 can have a distal end 114 and a proximal end 112, and each end 112, 114 can be closed. A proximal end closure mechanism 122 can close the proximal end 112, and a distal closure mechanism 124 can close the distal end 114. Closure mechanisms 122, 124 can be a crimped band or end cap such as is known in the art. Closure mechanisms 122, 124 can include a radiopaque material.

As illustrated in FIG. 1B, the proximal end closure mechanism 122 can be protrude into the outer occlusive sack 102 of the bowl shape as can be advantageous in some aneurysm treatments to avoid obstructing a blood vessel adjacent to the aneurysm with the proximal end closure mechanism 122.

FIG. 1C is an illustration of a view from a distal side of an example implant 100 in a deployed state such as the implants depicted in FIGS. 1A and 1B.

Figure 2:
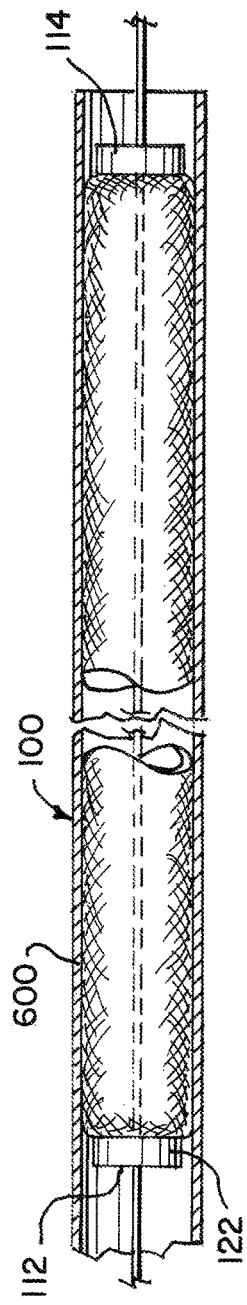
FIG. 2 is an illustration of an exemplary implant in a collapsed state in a microcatheter according to aspects of the present invention.

FIG. 2 is an illustration of an exemplary implant 100 in a collapsed state in a microcatheter 600. In the collapsed state, the implant 100 can have a substantially tubular shape having a proximal end 112, a distal end 114, and a braided or other flexible and expandable segment 110 extending between the proximal end 112 and the distal end 114. The braided segment 110 can include flexible wires braided to form a tube of wires that wrap helically around a center axis with roughly half of the wires wrapping clockwise, and the other half wrapping counterclockwise such that wires extending in opposite direction wrap over and under each other diagonally in an alternating fashion. When the implant 100 is in the collapsed state, the segment 110 can have sufficient flexibility to be delivered through the microcatheter 600, navigating torturous anatomical geometries, to be delivered to a treatment site.

The implant 100 can include a proximal end closure mechanism 122, a distal end closure mechanism 124, or both a proximal and a distal end closure mechanism 122, 124. The end closure mechanisms 122, 124 can include a radiopaque material, and can also serve as part of a means for delivering the implant 100 through the microcatheter 600 to the treatment site.

Figure 3C:
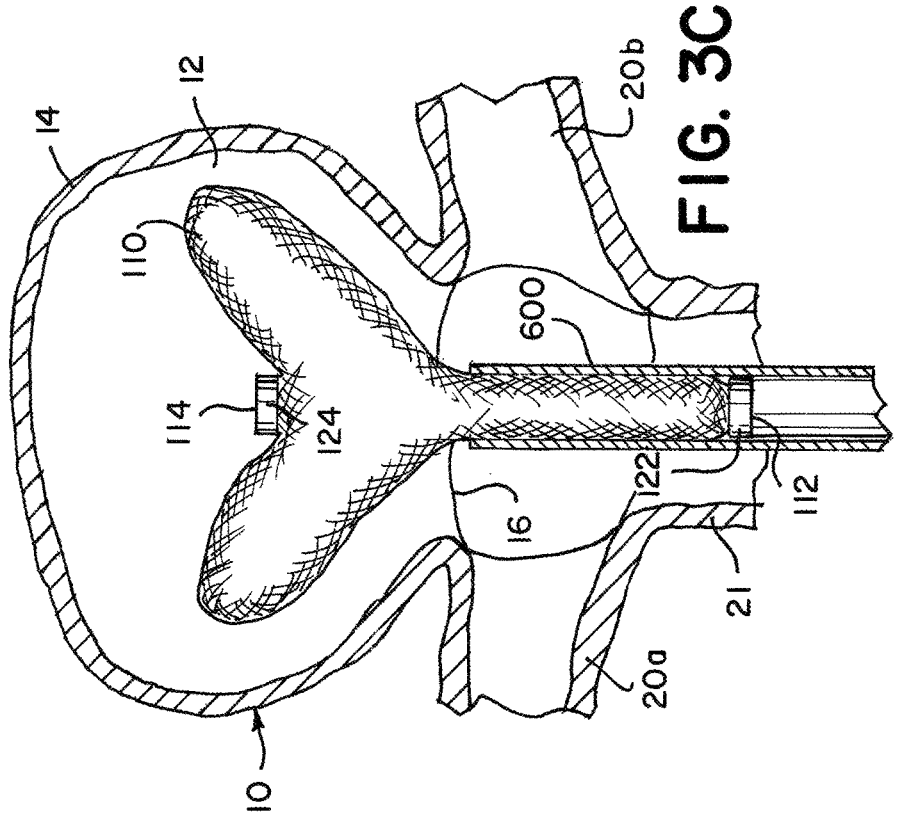

FIGS. 3A to 3F are illustrations of stages or steps that can occur during an implantation sequence of an exemplary implant 100. Starting with FIG. 3A, the implant 100 can be delivered to a treatment site by sliding the implant 100 distally in a collapsed state through a microcatheter 600. FIG. 3A depicts a distal end 114 of the implant 100 having a distal end closure mechanism 124 positioned within the microcatheter 600 near a neck 16 of an aneurysm 10 for deployment into an aneurysm sac 12. As illustrated in FIGS. 3A to 3F, the treatment site can include an aneurysm 10 positioned adjacent bifurcated blood vessel branches 20a, 20b, and the implant 100 can be delivered to the treatment site through a stem branch 21 feeding the bifurcated blood vessel branches 20a, 20b.

Figure 3B:
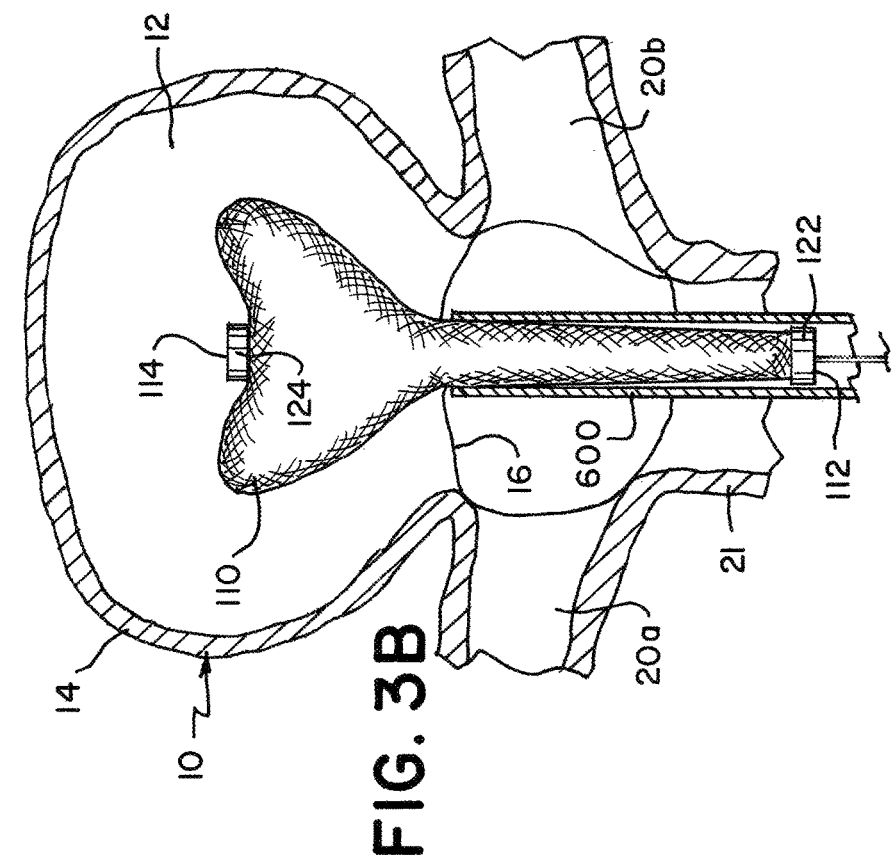

FIG. 3B illustrates the distal end 114 including the distal closure mechanism 124 pushed out of the microcatheter 600. The expelled portion of the braided segment 110 can expand as it exits the microcatheter 600. The braided segment 110 can include a memory shape material such as Nitinol, a Nitinol alloy, a polymer memory shape material, or other memory shape material having properties for reshaping as described herein. The braided segment 110 can be in a deformed shaped in the collapsed state and reshape based on a predetermined shape after exiting the microcatheter.

FIG. 3C illustrates further distal movement of the implant 100. As more of the braided segment 110 exits the microcatheter 600, the braided segment 110 can continue to expand. The braided segment 110 can also begin to invert to begin to form a trough at the distal end 114.

Figure 3D:
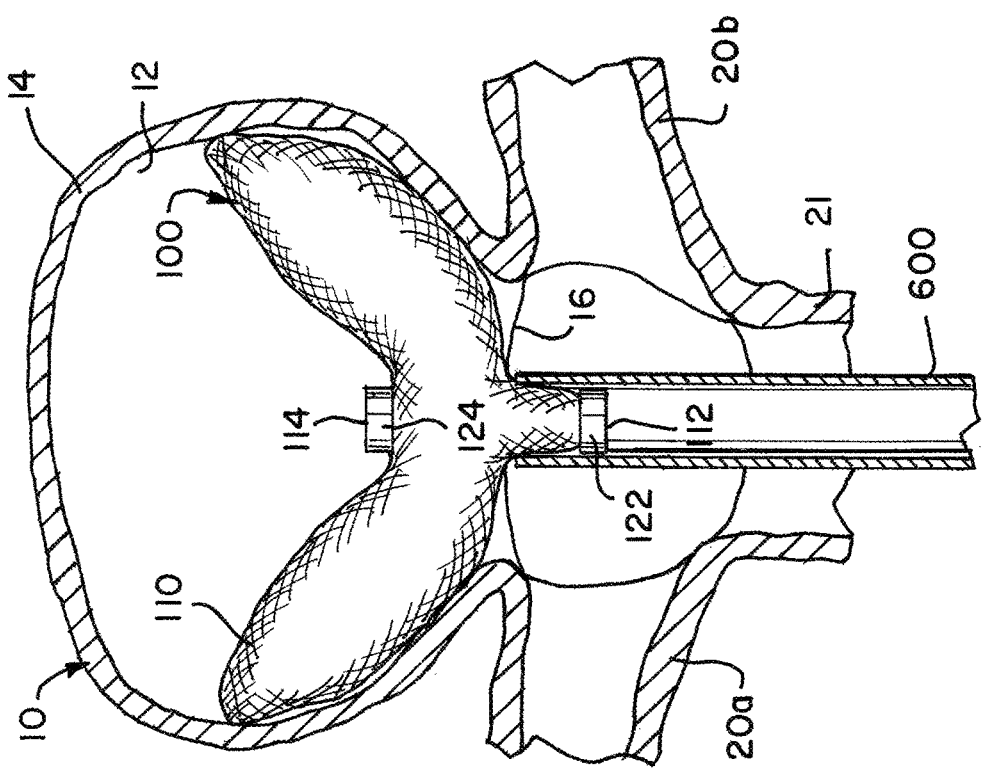

FIG. 3D illustrates more of the braided segment 110 exiting the microcatheter 600. As more of the braided segment 110 exits the microcatheter 600, the braided segment 110 can continue to expand and invert.

Figure 3E:
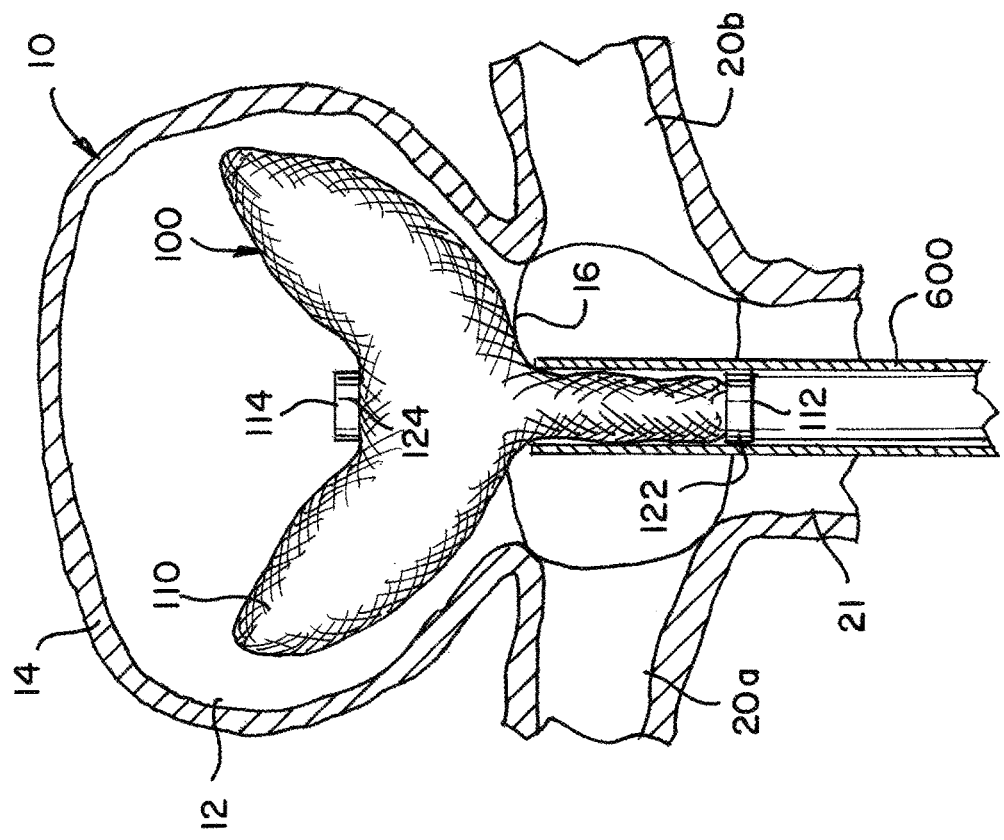

FIG. 3E illustrates the braided segment 110 almost entirely ejected from the microcatheter 600. As illustrated, the implant 100 can extend to an interior wall 14 of the aneurysm 10.

Figure 3F:
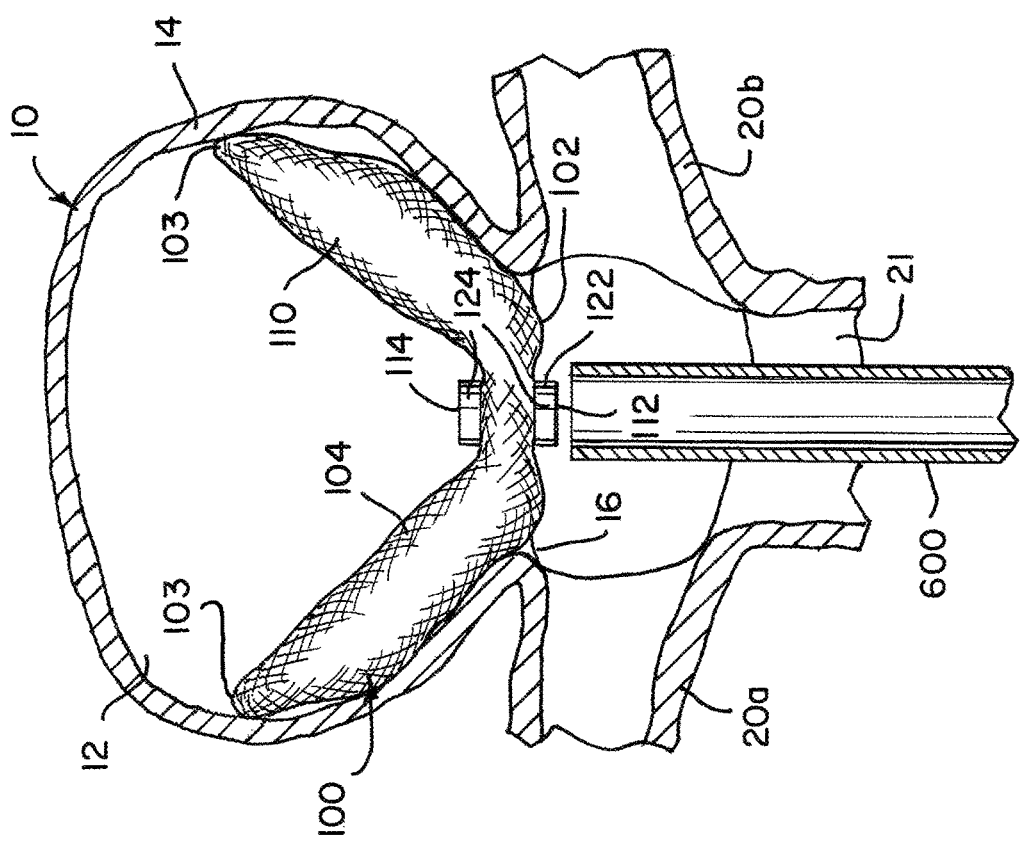

FIG. 3F illustrates the implant in a deployed state in the aneurysm 10. In the deployed state, the braided segment 110 can fold to form an outer occlusive sack 102 and an inner occlusive sack 104 separated by a fold 103. The outer occlusive sack 102 can extend radially from a proximal end 112 of the implant 100 to occlude at least a portion of the neck 16 of the aneurysm 10. In the deployed state, the outer occlusive sack 102 can deflect a blood flow from the aneurysm 10, diverting a blood flow from the aneurysm 10, slowing a blood from into the aneurysm 10, or any combination thereof.

In the deployed state, the outer occlusive sack 102 can extend to the aneurysm wall 14, and the outer occlusive sack 102 can provide a force against the aneurysm wall to maintain the implanted position of the implant 100 such that the implant 100 doesn't become dislodged and become ineffective at inhibiting blood flow into the aneurysm. The force of the outer occlusive sack 102 to the aneurysm wall 14 can be sufficient to maintain the position of the implant 100 within the aneurysm 10. For example, the braided segment 110 can be made of a memory shape material having a first, predetermined shape and a second, deformed shape. The braided segment 110 can be in the deformed shape when the implant 100 is in a collapsed state. When the implant 100 is in a deployed state within the aneurysm 10, the braided segment 110 can move to a third, deployed shape that is based at least in part on the first, predetermined shape and the anatomical geometry of the aneurysm 10. In the example, the first, predetermined shape can be sized larger than the wall 14 within the aneurysm sac 12; the braided segment 110 can move to extend to the wall 14; and the braided segment 110 can provide a force against the wall 14 as the properties of the memory shape material cause the braid 110 to attempt to open to the predetermined shape.

The implant 100 can include a proximal end closure mechanism 122 such as an end cap, band, or other mechanism as known in the art positioned near the proximal end 112 of the implant, closing the braided segment 110. The end closure mechanism 122 can be placed centrally in relation to the aneurysm neck 16 opening. As such, the implant 100 can define a substantially continuous occluding surface across the neck 16 of the aneurysm 10.

In the deployed state, the inner occlusive sack 104 can form a trough within the outer occlusive sack 102 such that the inner occlusive sack 104 nests within the outer occlusive sack 102. The distal end 114 of the implant 100 can be positioned centrally within the trough of the inner occlusive sack 104 and can be positioned centrally in relation to opening of the aneurysm neck 16. For an implant 100 including both a proximal end closure mechanism 122 and a distal end closure mechanism 124, when the implant 100 is in the deployed state and implanted in the aneurysm 10, the proximal end closure mechanism 122 and the distal end closure mechanism 124 can be aligned along an axis positioned centrally within the aneurysm neck 16, the axis perpendicular to a plane of the aneurysm neck 16.

The inner occlusive sack 104 and the outer occlusive sack 102 can together form a substantially bowl-shaped structure or a substantially enclosed bowl-shaped volume. The inner occlusive sack 104 and outer occlusive sack 102 can be separated by a fold 103. The fold 103 can define an annular ridge of the bowl-shaped structure or volume. The fold 103 can be positioned to appose an annular surface of the aneurysm wall 14. The bowl-shaped structure defined by the braided mesh 110 can have a substantially contiguous surface extending radially from the proximal end 112 outwardly across the aneurysm neck 16 and upwardly apposed to the aneurysm wall 14, then folding down and radially inward forming a trough that converges at the distal end 114 of the braided mesh 110. A first portion of the braided segment 110 can be capable of self-expanding to form the outer occlusive sack 102 and a second portion of the braided segment 110 can be capable of self-inverting to form the inner occlusive sack 104.

Figure 4A:
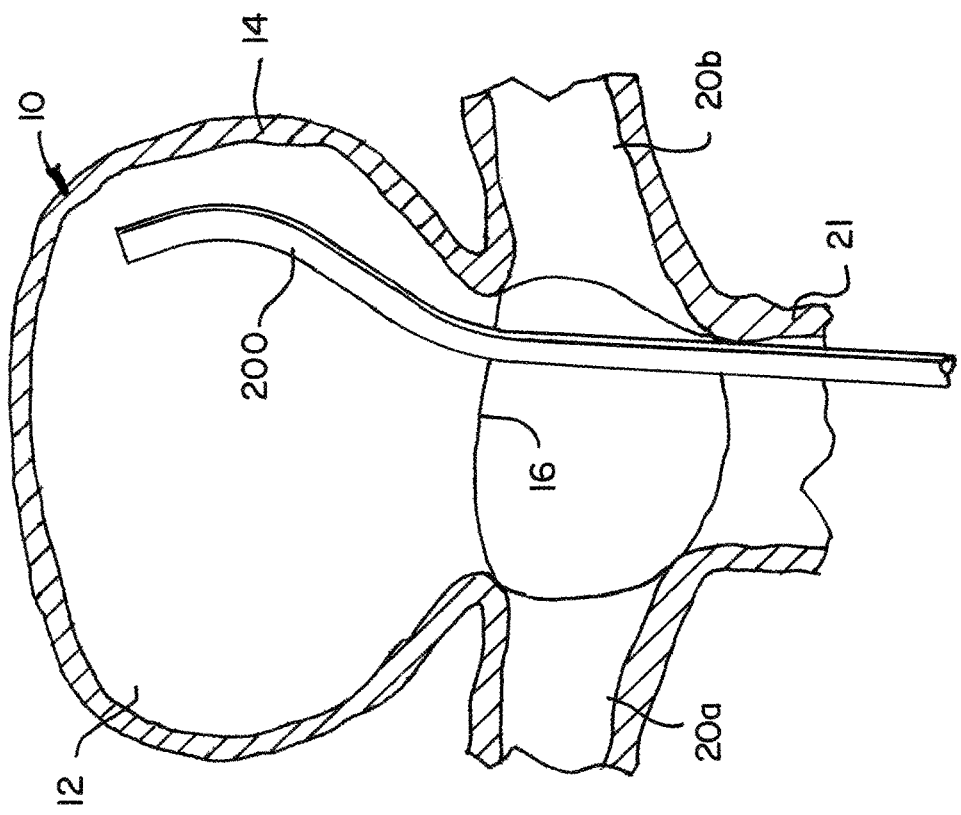

FIGS. 4A to 4G are illustrations of stages or steps that can occur during another example implantation sequence of an exemplary implant. FIG. 4A illustrates an embolic implant delivery catheter 200 having a distal end positioned within an aneurysm sac 12. FIG. 4B illustrates a microcatheter 600 positioned at a neck 16 of the aneurysm 10 having an implant 100 positioned within the microcatheter 600 near the aneurysm neck 16. Both the embolic implant delivery catheter 200 and the microcatheter 600 delivering the implant 100 can be delivered to the treatment site through a stem blood vessel 21 when treating an aneurysm at a bifurcation.

FIG. 4C illustrates the expansion of the braided segment 110 as the braided segment exits the microcatheter 600 like as illustrated in FIG. 3B. Referring to FIG. 4C, the expanding segment can begin to push against the embolic implant delivery catheter 200.

FIG. 4D illustrates the implant 100 in a deployed state within the aneurysm sac 12. The deployed implant can provide a force against the embolic implant delivery catheter 200, pushing the embolic implant delivery catheter 200 against the aneurysm wall 14. In this configuration, the embolic implant delivery catheter 200 can be "jailed" such that the force provided by the implant apposes the embolic implant delivery catheter 200 to the aneurysm wall 14 and holds the embolic catheter in place, inhibiting movement of the embolic implant delivery catheter 200 within the aneurysm sac 12.

FIG. 4E illustrates an embolic implant 300 such as an embolic coil being implanted into the aneurysm sac 12 via the embolic implant delivery catheter 200. The occlusive implant 100 in the deployed state within the aneurysm 10 can inhibit the embolic implant 300 from exiting through the neck 16 of the aneurysm 10. The embolic implant 300 can fill a bowl-shaped occlusive implant, providing a force from within the trough of the bowl pushing the occlusive implant outwardly against the aneurysm wall 14. The force from the embolic implant 300 can serve to maintain an implanted position of the occlusive implant 100 and the embolic implant 300 once treatment is completed.

FIG. 4F illustrates the embolic implant delivery catheter 200 being distally withdrawn following the completion of implanting the embolic implant 300.

FIG. 4G illustrates the aneurysm following extraction of the microcatheter 600 and the embolic implant delivery catheter 200, completing the implantation process.

FIG. 5 is an illustration of an exemplary implant absent a distal closure member implanted in a deployed state.

FIGS. 6A to 7B generally illustrate example attachment and delivery between delivery tube 400 and braid 110 for deploying and detaching braid 10 in aneurysm 10. The examples of FIGS. 6A to 7B depict one way that delivery tube 400 and braid 110 may be attached, however, as will be understood, any number of attachment means known in the art are contemplated as needed or required.

FIGS. 6A and 6B illustrate an implant having a locking member 454 affixed to the proximal end 112 of the braid 110 engaged with a delivery system at a distal end of the delivery tube 400. The delivery system shown includes a loop wire 458 extending through a lumen of the delivery tube 400 bent at a distal end to travel through an opening 459 of the locking member 454 and a locking rod 452 extending through the lumen of the delivery tube adjacent to the loop wire 458 and extending through a distal opening 460 of the loop wire 458. As illustrated in FIG. 6B, when the locking rod 452 is put through the distal opening 460 of the loop wire 458 and the loop wire 458 is fed through the opening 459 of the locking member 454, the braid 110 can be engaged with the distal end 414 of the delivery tube 400.

The delivery tube 400 can include a compressible portion 438 that can allow the delivery tube 400 to bend and/or flex. Such flexibility can assist tracking the implant 100 through a microcatheter and tortuous paths of a vasculature. The compressible portion 438 can also be delivered in a longitudinally compressed state that can extend to eject the braid 110 during deployment of the braid 110 as explained in relation to FIGS. 7A and 7B.

FIG. 7A illustrates the locking rod 452 being pulled proximally, exiting the distal opening 460 of the loop wire 458, and pulling free of the loop wire 458. Once the locking rod 452 has exited the distal opening 460 of the loop wire 458, at least a portion of the loop wire 458 near the distal opening 460 can reshape to exit the opening 459 of the locking portion 454.

As illustrated in FIG. 7B, once the loop wire exits the opening 459 of the locking portion 454, the braid 110 can disengage the delivery tube 400. The compressible portion 38 of the delivery tube 30 can expanded and spring forward, imparting a distally directed force E from the distal end 414 of the delivery tube 400 to the braid 110 to push the braid 110 away from the delivery tube 400 to insure a clean separation and delivery of the implant 100.

FIG. 8 illustrates another exemplary implant 100a being delivered by another delivery system. The delivery system can include a pusher tube 510 for engaging a distal end cap or band 124a of the implant 100a and a pusher bump 520 for engaging a proximal end 112a of the implant 100a. The implant 100a can have a substantially tubular shape sized so that a majority of the implant 100a is sized to fit within the pusher tube 510 and a distal end member 124a is sized larger than an inner dimension of the pusher tube 510. As illustrated in FIG. 8, distal translation of the pusher tube 510 can push the distal end member 124a distally, moving the implant 100a through the microcatheter 600 to a treatment site.

FIGS. 9A to 9C are illustrations of stages or steps that can occur during another example implantation sequence of an exemplary implant such as the implant 100a illustrated in FIG. 8. FIG. 9A illustrates a microcatheter 600 positioned at a neck 16 of the aneurysm 10 having an implant 100a positioned within the microcatheter 600 near the aneurysm neck 16. The implant 100a can be delivered to the treatment site through a stem blood vessel 21 when treating an aneurysm at a bifurcation, and the pusher tube 510 can be used to translate the implant 100a through the microcatheter 600.

FIG. 9B illustrates the implant 100a ejected from the microcatheter 600 and in the process of moving to a deployed state. The implant 100a can be pushed out of the pusher tube 510 and the microcatheter 600 by pushing a pusher bump 520 distally. The pusher bump 520 can be attached to a core wire or other elongated member and can be manufactured by means known in the art.

FIG. 9C illustrates the implant 100a in the deployed state similar to as described and illustrated in relation to examples herein.

Figure 10:
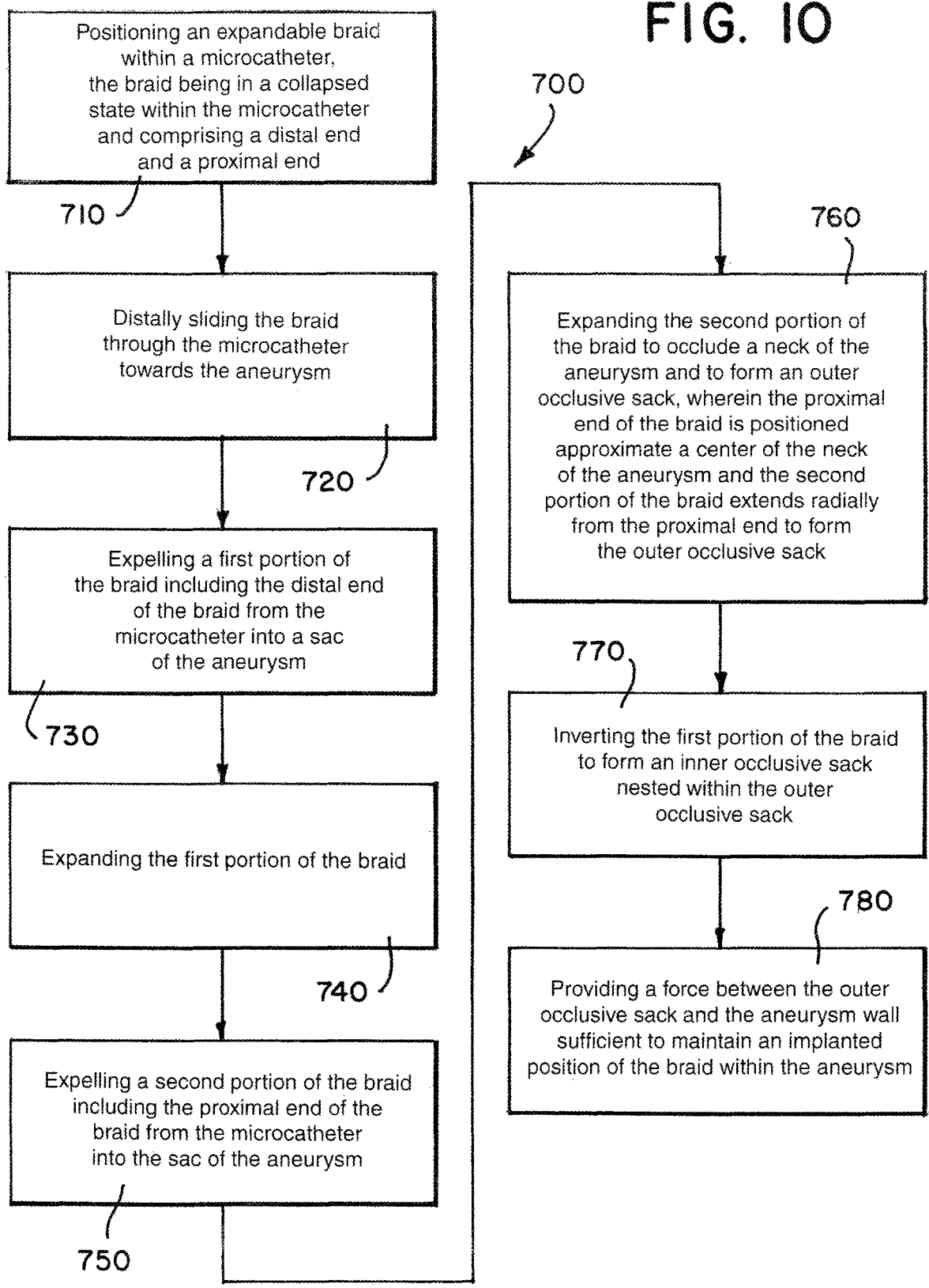
FIG. 10 is a flow diagram outlining example method steps that can be carried out during implantation of an occluding implant according to aspects of the present invention.

FIG. 10 is a flow diagram outlining example method steps that can be carried out during implantation of an occluding implant. The method steps can be implemented by any of the example means described herein or by any means that would be known to one of ordinary skill in the art.

Referring to a method 700 outlined in FIG. 10, in step 710 an expandable braid can be positioned within a microcatheter such that the expandable braid is in a collapsed state within the microcatheter. In step 720, the braid can be slid distally through the microcatheter towards an aneurysm. In step 730, a first portion of the braid that includes a distal end of the braid can be expelled from the microcatheter into a sac of the aneurysm. In step 740, the first portion of the braid can be expanded. In step 750, a second portion of the braid including a proximal end of the braid can be expelled from the microcatheter into the sac of the aneurysm. In step 760, the second portion of the braid can be expanded to occlude a neck of the aneurysm and to form an outer occlusive sack such that the proximal end of the braid is positioned near the center of the aneurysm neck and the second portion of the braid extends radially from the proximal end to form the outer occlusive sack. In step 770, the first portion of the braid can be inverted to form an inner occlusive sack nested within the outer occlusive sack. In step 780, the outer occlusive sack can provide a force against the aneurysm wall that is sufficient to maintain an implanted position of the expanded braid within the aneurysm.

The descriptions contained herein are examples of embodiments of the invention and are not intended in any way to limit the scope of the invention. As described herein, the invention contemplates many variations and modifications of the device for occluding an aneurysm, including alternative geometries of elements and components described herein, utilizing any number of known means for braiding, knitting, weaving, or otherwise forming the expandable section as is known in the art, utilizing any of numerous materials for each component or element (e.g. radiopaque materials, memory shape materials, etc.), utilizing additional components including components to deliver an implant to a treatment site or eject an implant from a delivery catheter, or utilizing additional components to perform functions not described herein, for example. These modifications would be apparent to those having ordinary skill in the art to which this invention relates and are intended to be within the scope of the claims which follow.

What is claimed is:

1. A device for occluding an aneurysm comprising:
    an implant movable from a collapsed state to a deployed state, the implant comprising a proximal end, a distal end, and a braided segment forming a substantially continuous braided structure between the proximal end and the distal end,
    wherein in the deployed state, the implant comprises:
        an outer occlusive sack extending from the proximal end of the implant and capable of occluding an aneurysm neck;
        an inner occlusive sack extending form the distal end of the implant and forming a trough within the outer occlusive sack; and
        a fold in the braided segment positioned between the outer occlusive sack and the inner occlusive sack,
    wherein the implant is capable of anchoring within the aneurysm such that a majority of a sac of the aneurysm is unoccupied by a substantially enclosed volume defined by the implant in the deployed state between the outer occlusive sack and the inner occlusive sack,
    wherein the braided segment comprises a memory shape material, the braided segment comprising a first, predetermined shape and a second, deformed shape,
    wherein the braided segment is in the second, deformed shape when the implant is in the collapsed state, and
    wherein the braided segment moves to a third, deployed shape when the implant is in the deployed state, the third, deployed shape based at least in part on the predetermined shape and a curvature of an aneurysm wall,
    wherein, in the first, predetermined shape, the fold defines an annular ridge,
    wherein the implant further comprising a radiopaque marker band encircling the distal end of the implant, and
    wherein, in the first, predetermined shape, the radiopaque marker band extends approximate a plane defined by the annular ridge.

2. The device of claim 1 wherein a first portion of the braided segment is capable of self-expanding to form the outer occlusive sack and a second portion of the braided segment is capable of self-inverting to form the inner occlusive sack.

3. The device of claim 1 wherein in the collapsed state, the implant is sized to be delivered to the aneurysm through a microcatheter.

4. The device of claim 1 wherein one or more of the proximal end of the implant or the distal end of the implant is closed.

5. The device of claim 4 wherein one or more of the distal end or the proximal end is closed by one of a band, an end cap, or heat set.

6. The device of claim 1 wherein in the deployed state, the outer occlusive sack is capable of sealing the aneurysm neck to at least one of deflect, divert, and slow a flow into the aneurysm.

7. The device of claim 1 wherein in the deployed state, the distal end and proximal end of the implant are each positioned along an axis approximately perpendicular to a plane defined by the aneurysm neck and approximate a center of the aneurysm neck.

8. The device of claim 1 wherein the implant is implantable in an aneurysm adjacent bifurcated blood vessel branches, and wherein the implant is deliverable to the aneurysm through a stem branch feeding the bifurcated blood vessel branches.

9. The device of claim 1 wherein, in the predetermined shape, the braided segment comprises an annular ridge defined by the fold that is larger circumferentially than a maximum circumference of the aneurysm sac.

10. The device of claim 1 wherein, in the first, predetermined shape, the inner occlusive sack substantially conforms to the outer occlusive sack.

11. An implant for treating an aneurysm comprising a braided mesh,
    wherein the braided mesh is movable to an implanted configuration, the braided mesh comprising a substantially contiguous surface defining a substantially enclosed, bowl-shaped volume in the implanted configuration, and
    wherein the implant is capable of anchoring within the aneurysm such that a majority of a sac of the aneurysm is unoccupied by the bowl-shaped volume,
    wherein the braided mesh comprises a memory shape material, the braided mesh comprising a first, predetermined shape and a second, deformed shape, wherein the braided mesh is in the second, deformed shape is sized to traverse vasculature,
    wherein the braided mesh moves to a third, deployed shape when the implant is in a deployed state, the third, deployed shape based at least in part on the predetermined shape and a curvature of an aneurysm wall, wherein the implant further comprising a radiopaque marker band encircling a distal end of the implant within a trough of the bowl-shaped volume, and wherein, in the first, predetermined shape, the radiopaque marker band extends approximate a plane defined by an annular ridge of the bowl-shaped volume.

12. The implant of claim 11 wherein the braided mesh is movable from a substantially tubular configuration having a first end and a second end to the implanted configuration, and wherein, in the implanted configuration, the first end and the second end are each positioned approximate a center of the bowl-shaped volume and a fold in the braided mesh defines an annular ridge of the bowl-shaped volume.

13. The implant of claim 11, wherein the braided mesh comprises a memory shape material, the braided mesh comprising a first, predetermined shape and a second, deformed shape, wherein the braided mesh is in the second, deformed shape is sized to traverse vasculature, wherein the braided mesh moves to a third, deployed shape when the implant is in the deployed state, the third, deployed shape based at least in part on the predetermined shape and a curvature of an aneurysm wall, wherein, in the first, predetermined shape, an annular ridge of the bowl-shaped volume that is larger circumferentially than a maximum circumference of the aneurysm sac.

14. The implant of claim 11, wherein the braided mesh comprises a memory shape material, the braided mesh comprising a first, predetermined shape and a second, deformed shape, wherein the braided mesh is in the second, deformed shape is sized to traverse vasculature, wherein the braided mesh moves to a third, deployed shape when the implant is in the deployed state, the third, deployed shape based at least in part on the predetermined shape and a curvature of an aneurysm wall, and wherein, in the first, predetermined shape, an inner occlusive sack of the bowl-shaped volume substantially conforms to an outer occlusive sack of the bowl-shaped volume and a fold separating the inner occlusive sack and outer occlusive sack defines an annular ridge of the bowl-shaped volume.

* * * * *